(12) United States Patent
Schuele et al.

(10) Patent No.: US 7,858,395 B2
(45) Date of Patent: Dec. 28, 2010

(54) ANTIBODIES FOR USE IN IDENTIFYING AND/OR SCORING PROSTATE CANCER AND ANDROGEN RECEPTOR-DEPENDENT GENE EXPRESSION CONTROL

(75) Inventors: Roland Schuele, Weisweil (DE); Erich Metzger, Neuf-Brisach (FR); Reinhard Buettner, Bonn (DE)

(73) Assignees: Universitaetsklinikum Freiburg, Freiburg (DE); Rheinische Friedrich-Wilhelms-Universitaet Bonn, Bonn (DE)

( * ) Notice: Subject to any disclaimer, the term of this patent is extended or adjusted under 35 U.S.C. 154(b) by 111 days.

(21) Appl. No.: 11/995,387

(22) PCT Filed: Jul. 13, 2006

(86) PCT No.: PCT/EP2006/006881

§ 371 (c)(1),
(2), (4) Date: May 28, 2008

(87) PCT Pub. No.: WO2007/006581

PCT Pub. Date: Jan. 18, 2007

(65) Prior Publication Data

US 2009/0104196 A1    Apr. 23, 2009

(30) Foreign Application Priority Data

Jul. 13, 2005  (EP) .................................. 05015253
Jul. 29, 2005  (EP) .................................. 05016576

(51) Int. Cl.
*G01N 33/53* (2006.01)
(52) U.S. Cl. ........................ 436/501; 436/518; 435/7.23
(58) Field of Classification Search ........................ None
See application file for complete search history.

(56) References Cited

U.S. PATENT DOCUMENTS

2004/0121413 A1 * 6/2004 Aebersold et al. .......... 435/7.23

FOREIGN PATENT DOCUMENTS

| EP | 1693062 | 8/2006 |
|---|---|---|
| EP | 1693383 | 8/2006 |
| WO | 2006/071608 | 7/2006 |

OTHER PUBLICATIONS

Y. Shi et al., "Histone Demethylation Mediated by the Nuclear Amine Oxidase Homolog LSD1" *Cell* vol. 119, pp. 941-953 (2004).
E. Metzger et al., "LSD1 demethylates repressive histone marks to promote androgen-receptor-dependent transcription" *Nature* vol. 437, pp. 436-439 (2005).
D.B. Seligson et al., "Global histone modification patterns predict risk of prostate cancer recurrence", Nature, vol. 435, pp. 1262-1266 (2005).
M. Breslow et al. "Latent carcinoma of prostate at autopsy in seven areas" *Int. J. Cancer* vol. 20, pp. 680-688 (1977).
A.C.B. Cato et al., "The androgen receptor as a mediator of gene expression and signal transduction pathways" *Trends Endocrinol. Metab.* vol. 9, pp. 150-154 (1998).
S.R. Denmeade et al., "A history of prostate cancer treatment" *Nat. Rev. Cancer* vol. 2, pp. 389-396 (2002).
J.W. Waterbor et al., "Prostate Cancer Screening (United States)" *Cancer Causes and Control* vol. 6, pp. 267-274 (1995).
C.K. Glass et al., "The coregulator exchange in transcriptional functions of nuclear receptors" *Genes Dev.* vol. 14, pp. 121-141 (2000).
B.D. Strahl et al., "The language of covalent histone modifications" *Nature* vol. 403, pp. 41-45 (2000).
Y. Shi et al., "Coordinated histone modifications mediated by a CtBP co- repressor complex" *Nature* vol. 422, pp. 735-738 (2003).
M.A. Hakimi et al. "A candidate X-linked mental retardation gene is a component of a, new family of histone deacetylase-containing complexes" *J. Biol. Chem.* vol. 278, pp. 7234-7239 (2003).
M.A. Hakimi et al. "A core-BRAF35 complex containing histone deacetylase mediates repression of neuronal-specific genes" *Proc. Natl. Acad. Sci. USA* vol. 99, pp. 7420-7425 (2002).
S. Eimer et al., "Loss of *spr*-5 bypasses the requirement for the *C. elegans* presenilin *sel*-12 by derepressing *hop*-1" *EMBO J.* vol. 21, pp. 5787-5796 (2002).
J. M. Müller et al., "FHL2, a novel tissue-specific coactivator of the androgen receptor" *EMBO J.* vol. 19, pp. 359-369 (2000).
J. M. Müller et al., "The transcriptional coactivator FHL2 transmits Rho signals from the cell membrane into the nucleus" *EMBO J.* vol. 21, pp. 736-748 (2002).
Y. Shang et al., "Formation of the androgen receptor transcription complex" *Molecular Cell* vol. 9, pp. 601-610 (2002).

(Continued)

*Primary Examiner*—Misook Yu
(74) *Attorney, Agent, or Firm*—Greenblum and Bernstein, P.L.C.

(57) ABSTRACT

The invention relates to antibodies for use for modulating the activity of the lysine-specific demethylase (LSD1) in a mammal and to pharmaceutical and diagnostical compositions comprising such antibodies. The invention also relates to a method for identifying and/or scoring prostate carcinomas. Furthermore, the invention relates to the use of at least one siRNA ("short interfering RNA") and/or at least one anti-LSD1 antibody for modulating the activity of the lysine-specific demethylase (LSD1) in a mammal or for the manufacture of a medicament for modulating the activity of the lysine-specific demethylase (LSD1) in a mammal. The invention also relates to a pharmaceutical composition for controlling the androgen receptor-dependent gene expression, comprising an effective dose of at least one siRNA and/or at least one anti-LSD1 antibody suitable for modulating the activity of the lysine-specific demethylase (LSD1) in a mammal. The invention also relates to a method for controlling the androgen receptor-dependent gene expression in a mammal, said process comprising the step of administering to said mammal, on a suitable route, an effective dose of a pharmaceutical composition modulating an activity of the lysine-specific demethylase (LSD1) in a mammal.

6 Claims, 11 Drawing Sheets

OTHER PUBLICATIONS

L. Shatkina et al., "The cochaperone Bag-1L enhances androgen receptor action via interaction with the $NH_2$-terminal region of the receptor" *Mol. Cell. Biol.* vol. 23, pp. 7189-7197 (2003).

Z. Kang et al., "Involvement of proteasome in the dynamic assembly of the androgen receptor transcription complex" *J. Biol. Chem.* vol. 277, pp. 48366-48371 (2002).

E. Metzger et al., "A novel inducible transactivation domain in the androgen receptor: implications for PRK in prostate cancer" *EMBO J.* vol. 22, pp. 270-280 (2003).

M. Wiznerowicz et al., "Conditional suppression of cellular genes: lentivirus vector-mediated drug-inducible RNA interference" *J. Virol.* vol. 77, pp. 8957-8961 (2003).

M.W. Pfaffl et al. "Relative expression software tool (REST©) for group-wise comparison and statistical analysis of relative expression results in real-time PCR" *Nucleic Acids Res.* vol. 30, e36 (2002).

T.E. O'Neill et al., "Nucleosome arrays inhibit both initiation and elongation of transcripts by bacteriophage T7 RNA polymerase" *J. Mol. Biol.* vol. 223, pp. 67-78 (1992).

R. Schüle et al., "Functional antagonism between oncoprotein c-Jun and the glucocorticoid receptor" *Cell* vol. 62, pp. 1217-1226 (1990).

G. Verrijdt et al., "Functional interplay between two response elements with distinct binding characteristics dictates androgen specificity of the mouse sex-limited protein enhancer" *J. Biol. Chem.* vol. 277, pp. 35191-35201 (2002).

Z. Sun et al., "Androgen receptor-associated protein complex binds upstream of the androgen-responsive elements in the promoters of human prostate-specific antigen and kallikrein 2 genes" *Nucleic Acids Res.* vol. 25, pp. 3318-3325 (1997).

T.R. Brummelkamp et al., "A system for stable expression of short interfering RNAs in mammalian cells" *Science* vol. 296, pp. 550-553 (2002).

E.F. Greiner et al., "Differential ligand-dependent protein-protein interactions between nuclear receptors and a neuronal-specific cofactor" *Proc. Natl. Acad. Sci. USA* vol. 97, pp. 7160-7165 (2000).

R. Schüle et al., "Jun-Fos and receptors for vitamins A and D recognize a common response element in the human osteocalcin gene" *Cell* vol. 61, pp. 497-504 (1990).

R. Schneider et al., "Direct binding of INHAT to H3 tails disrupted by modifications" *J. Biol. Chem.* vol. 279, pp. 23859-23862 (2004).

G. Rigaut et al., "A generic protein purification method for protein complex characterization and proteome exploration" *Nat. Biotechnol.* vol. 17, pp. 1030-1032 (1999).

Abstract of T. Bocker et al., "In vitro and ex vivo expression of nucleolar proteins B23 and p120 in benign and malignant epithelial lesions of the prostate" *J. Modern Pathology* vol. 8, No. 3, pp. 226-231 (1995).

* cited by examiner a b a b

ANTIBODIES FOR USE IN IDENTIFYING AND/OR SCORING PROSTATE CANCER AND ANDROGEN RECEPTOR-DEPENDENT GENE EXPRESSION CONTROL

The present invention relates to specific antibodies modulating the activity of the lysine-specific demethylase LSD1 in a mammal which may be used for identifying and/or scoring prostate cancer.

The present invention also relates to the use of at least one siRNA ("short interfering RNA") and/or at least one anti-LSD1 antibody for modulating the activity of the lysine-specific demethylase (LSD1) in a mammal or for the manufacture of a medicament for modulating the activity of the lysine-specific demethylase (LSD1) in a mammal. The invention also relates to a pharmaceutical composition for controlling the androgen receptor-dependent gene expression, comprising an effective dose of at least one siRNA and/or at least one anti-LSD1 antibody suitable for modulating the activity of the lysine-specific demethylase (LSD1) in a mammal. The invention also relates to a method for controlling the androgen receptor-dependent gene expression in a mammal, said process comprising the step of administering to said mammal, on a suitable route, an effective dose of a pharmaceutical composition modulating an activity of the lysine-specific demethylase (LSD1) in a mammal.

The androgen receptor (AR) is a member of the steroid hormone receptor family of transcription factors which regulate diverse biological functions including cell growth and differentiation, development, homeostasis and various organ functions in a mammal, particularly in a human. By binding suitable ligands like androgens to the ligand binding domain, functions of the AR are activated which are essential for the differentiation, development and maintenance of male or female reproductive organs and non-reproductive organs (as, for example, the prostate or the mammae).

Transcriptional regulation by nuclear receptors such as the androgen receptor (AR) involves interaction with multiple factors that act in both a sequential and combinatorial manner to reorganize chromatin[5]. Central to this dynamic reorganization is the modification of core histones. The N-terminal tails of histones are subject to various covalent modifications such as acetylation, phosphorylation, ubiquitination and methylation by specific chromatin-modifying enzymes[6]. Histone methylation at specific lysine residues is linked to both transcriptional repression and activation[6]. When searching for new AR interacting proteins, Lysine specific demethylase 1 (LSD1)[7] was found to be one example of the chromatin-modifying enzymes.

LSD1 contains a centrally located swirm domain which functions as a putative protein-protein interaction motif, and also contains a C-terminal amine oxidase (AO) domain that harbours the demethylase activity[7] (FIG. 1b). Endogenous LSD1 and AR associate in vivo in androgen-sensitive tissues such as testis (FIG. 1a). To map the interaction domain between LSD1 and AR in vitro, GST pull-down analyses with labelled LSD1 and mutants thereof together with GST-AR fusion proteins were performed. As shown in FIG. 1b, full-length LSD1, as well as the swirm domain (LSD1 175-246) and the AO domain (LSD1 247-852) associate with either the N-terminus (NTD), the DNA binding domain (DBD), or the ligand-binding domain (LBD) of AR. In contrast, neither the N-terminus of LSD1 (LSD1 1-174) nor the GST control interact with AR.

siRNA (short interfering RNA) are double-stranded RNA having about 21 to 23 nucleotides. If one strand thereof is complementary to an active mRNA in an organism, such a strand combines to the mRNA to form a RNA-induced silencing complex (RISC), resulting into a decomposition of said RNA by ribonuclease H and preventing its translation.

It was now surprisingly found that the demethylating enzyme LSD1 is expressed ubiquitously in human and murine fetal and adult tissues (FIG. 2a and data not shown). Furthermore, it was also detected that LSD1 is found in the same cells (and in the same sub-cellular areas) where the AR is located (FIGS. 2c, d). In the course of the research resulting into the present invention, the above (and further) findings led to the conclusion that the demethylating enzyme LDS1 may exert a controlling influence on androgen-dependent gene expression. Furthermore, it was found that specific siRNA and/or a LSD1 antibody may be used to control demethylase activity and thereby regulate the AR. Thus, a specific modulation of LSD1 activity might by a promising therapeutic target in tissues where the AR plays a pivotal physiological role.

Prostate cancer represents the most frequent malignant disease in men worldwide and the second leading cause of death from malignant tumors[3]. The incidence is strongly related to age: While being very rare below the age of 50 years the incidence rises to approximately 1150 cases per 100,000 males at the age of 80[4]. In parallel there is a significant increase in overall incidence. In the year 2000, there were 92,000 new cases and it is estimated that this figure will increase to 120,000 in the year 2020[3].

A peculiarity of prostate cancer is a relatively high portion of latent cancers that will not progress to clinically manifested disease and therefore require no therapy[1]. These tumors also show an age-dependent increase in incidence from 10% at the age of 50 to 60% in patients older than 80 years. It is estimated that only ⅓ to ⅕ of all prostate cancers progress to clinically relevant disease. These data highlight the clinical need to distinguish reliably between progressive and non-progressive carcinomas.

The clinical outcome of prostate cancer is strongly related to its differentiation and malignancy grade. In particular the Gleason scoring system, presently the most common prostate cancer scoring system, makes use of the increasingly disturbed normal tissue architecture in high grade carcinomas. However, the Gleason scoring system reveals significant inter-observer variation and is difficult to assess reliably in small biopsies. Although a large number of tumor-suppressor genes and oncogenes have been identified and analysed in prostate cancers, the molecular mechanisms, which lead to dissolution of glandular structures and invasion, are largely unknown. Thus, there is a clinical need for molecular factors discriminating between progressive and non-progressive carcinomas in biopsies.

We have recently observed that the androgen receptor-interacting protein LSD1 is overexpressed in dedifferentiated and progressive prostate carcinomas. Therefore, we analysed the expression of LSD1 in a cohort of 99 patients with prostate cancers of different biology. Group A patients had tumours with clinical stages of T2c or less and Gleason scores of 6 or less (low risk cancers). Group B patients had tumours with any clinical stage and Gleason score 8, 9, or 10 (high risk cancers). 29 different antigens were stained by immunohistochemistry in these cancers and quantified according to the number of positive cancer cells and the staining intensity on a numerical scale from 0 to 300. These studies identified LSD1 as the most discriminatory antigen (p<0.001) that was strongly overexpressed in carcinomas of the high risk group.

From these data we claim that immunohistochemical staining of LSD1 in prostate carcinomas is the most discriminatory surrogate marker to identify high risk carcinomas at risk for systemic progression.

The invention relates to antibodies for use for modulating the activity of the lysine-specific demethylase (LSD1) in a mammal.

The invention also relates to the use of at least one siRNA for modulating the activity of the lysine-specific demethylase (LSD1) in a mammal.

Furthermore, the invention also relates to antibodies for use for the manufacture of a diagnostic agent for modulating the activity of the lysine-specific demethylase (LSD1) in a mammal.

Furthermore, the invention relates to the use of at least one siRNA for the manufacture of a medicament for modulating the activity of the lysine-specific demethylase (LSD1) in a mammal.

The invention also relates to a pharmaceutical or diagnostical composition comprising at least one antibody according to the subsequent detailed description, optionally together with at least one of pharmaceutically or diagnostically acceptable carriers, diluents and/or auxiliary substances.

The invention also relates to the use of at least one anti-LSD1 antibody for modulating the activity of the lysine-specific demethylase (LSD1) in a mammal.

The invention also relates to a method for identifying and/or scoring prostate carcinomas, said method comprising the step of immunostaining tissues, cells, body fluids and/or protein extracts relating to prostate cancer including employing anti-LSD1 antibodies, and quantifying the LSD1 amount in said tissues, cells, body fluids and/or protein extracts.

Furthermore, the invention also relates to the use of at least one anti-LSD1 antibody for the manufacture of a medicament for modulating the activity of the lysine-specific demethylase (LSD1) in a mammal.

The invention also relates to the use of at least one antibody for identifying and/or scoring prostate carcinomas in a mammal.

The invention also relates to the use of at least one antibody for the manufacture of a diagnostic agent for identifying and/or scoring prostate carcinomas in a mammal.

The invention also relates to the use of at least one siRNA in combination with at least one anti-LSD1 antibody for modulating the activity of the lysine-specific demethylase (LSD1) in a mammal.

Furthermore, the invention relates to the use of at least one siRNA in combination with at least one anti-LSD1 antibody for the manufacture of a medicament for modulating the activity of the lysine-specific demethylase (LSD1) in a mammal.

Furthermore, the invention relates to a pharmaceutical composition for controlling the AR-dependent gene expression comprising an effective dose of at least one siRNA suitable for modulating the activity of the lysine-specific demethylase (LSD1) in a mammal.

The invention also relates to a pharmaceutical composition for controlling the androgen receptor-dependent gene expression comprising an effective dose of at least one anti-LSD1 antibody suitable for modulating the activity of the lysine-specific demethylase (LSD1) in a mammal.

In addition, the invention relates to a pharmaceutical composition for controlling the AR-dependent gene expression comprising an effective dose of at least one siRNA and of at least one anti-LSD1 antibody suitable for modulating the activity of the lysine-specific demethylase (LSD1) in a mammal.

The invention also relates to a method for controlling the androgen receptor-dependent gene expression in a mammal, said process comprising the step of administering to said mammal, on a suitable route, an effective dose of a pharmaceutical composition modulating an activity of the lysine-specific demethylase (LSD1) in a mammal.

The invention also relates to siRNA capable of targeting LSD1 DNA sequences involved in the modulation of the activity of the lysine-specific demethylase (LSD1) in a mammal.

The invention also relates to an anti-LSD1 antibody capable of targeting an epitope in the LDS1 protein of a mammal.

The invention is further explained in the following description by referring to the Figures. However, the embodiments addressed in the Figures are considered to only exemplify the invention and should not be construed to restrict the invention. In the Figures, FIG. 1 shows the following: LSD1 interacts with AR in vivo and in vitro. a, AR co-immunoprecipitates with LSD1. Extracts from mouse testis were immunoprecipitated with α-LSD1 or α-cyclin A antibodies and rabbit IgG as control. Western blots were decorated with α-AR and α-LSD1 antibodies. b, GST pull-down assays were performed with labelled LSD1 mutants and the corresponding bacterially expressed GST-AR fusion proteins. GST, GST-Nix1, GST-ROR☐, and GST ERβ-NTD proteins were used as control. (NTD; N-terminal domain, DBD; DNA-binding domain, LBD; ligand-binding domain).

FIG. 2 shows LSD1 expression analyses: a, Expression of LSD1 mRNA in human tissues was examined by Northern blot analyses on a Human Multiple Tissue Expression Array. b, Immunohistochemical staining of LSD1 and AR in human normal and tumour prostate. LSD1 (B, E, H) and AR (C, F, I) immunoreactivity is detected in the secretory epithelium of normal prostate (B, C, arrows) and tumour cells (E, F, H, I, arrows). Hematoxilin-eosin (HE) stained sections are shown (A, D, G). All sections were taken from the same radical prostatectomy specimen. Magnification: ×250.

FIG. 3 shows how LSD1 interacts with chromatin. LNCaP cells were incubated with or without R1881 (a, b, c), treated with or without pargyline (b), or transfected with siRNA (c). ChIP or Re-ChIP was performed with the indicated antibodies. The precipitated chromatin was amplified by PCR using primers flanking the promoter region (ARE I+II), the middle region (middle), the enhancer region (ARE III), exon 4 of the PSA gene, or the promoters of the GAPDH and U6 genes. siRNA-mediated knockdown of LSD1 is verified by Western blot analysis (c, right panel) using α-AR and α-LSD1 antibodies. d, Native nucleosomes from HeLa cells were incubated in the presence of R1881 with either purified TAP, TAP-LSD1/AR, or TAP-LSD1 complexes with or without pargyline. Western blots were decorated with the indicated antibodies (left panel). The presence of LSD1 and AR in the TAP purified protein complexes was verified by Western blotting using αAR and α-LSD1 antibodies (right panel).

FIG. 4 shows how LSD1 controls AR-induced transcriptional activity and cell proliferation. 293 (a, b, c), or LNCaP (e) cells were transfected with the indicated AR-dependent reporters in presence of AR expression plasmid (a-c). Cells were treated with or without R1881, pargyline, deprenyl, or clorgyline. LSD1-induced ligand-dependent activation of AR (a) is mediated by the AO domain (LSD1 247-852, b) and blocked by monoamine oxidase inhibitors (c). Pargyline also reduces endogenous PSA gene expression in LNCaP cells as quantified by qRT-PCR (d). In LNCaP cells, siRNA-mediated LSD1 knockdown reduces AR activity (e, left panel). LSD1 knockdown inhibits R1881-induced LNCaP cell proliferation (f, left panel). Knockdown of LSD1 is verified by immunofluorescence (e, right panel, arrows) and Western blot analysis (f, right panel) using α-AR and α-LSD1 antibodies. Bars represent mean±SD (n>5).

FIG. 5 shows: a, Coomassie blue staining reveals that LSD1 (arrow) is co-purified with TAP-FHL2 (arrow) during tandem affinity purification. Asterisks re-present proteins that specifically co-purify with TAP-FHL2 but not with the TAP control. b, Western blot analysis using α-LSD1 antibody show that bacterially expressed and purified His-LSD1 interacts with bacterially expressed and purified GST-AR fusion proteins but not with the GST, GST-Nix1, GST-RORβ, and GST ERβ-NTD control proteins. (NTD; N-terminal domain, DBD; DNA-binding domain, LBD; ligand-binding domain).

Figure 8:
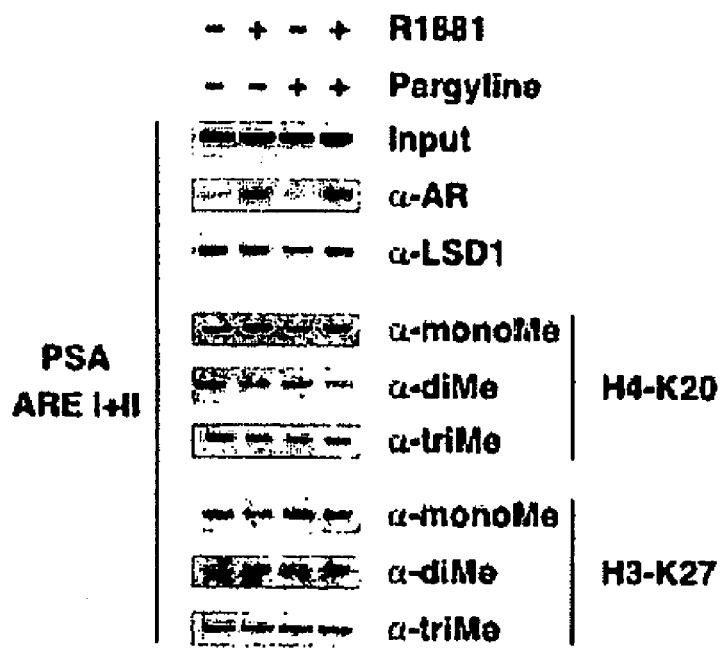

FIG. 8 LNCaP cells were incubated with or without R1881 and treated with or without pargyline. ChIP assays were performed with the indicated antibodies. The precipitated chromatin was amplified by PCR using primers flanking the promoter region (ARE I+II) of the PSA gene.

Figure 3:
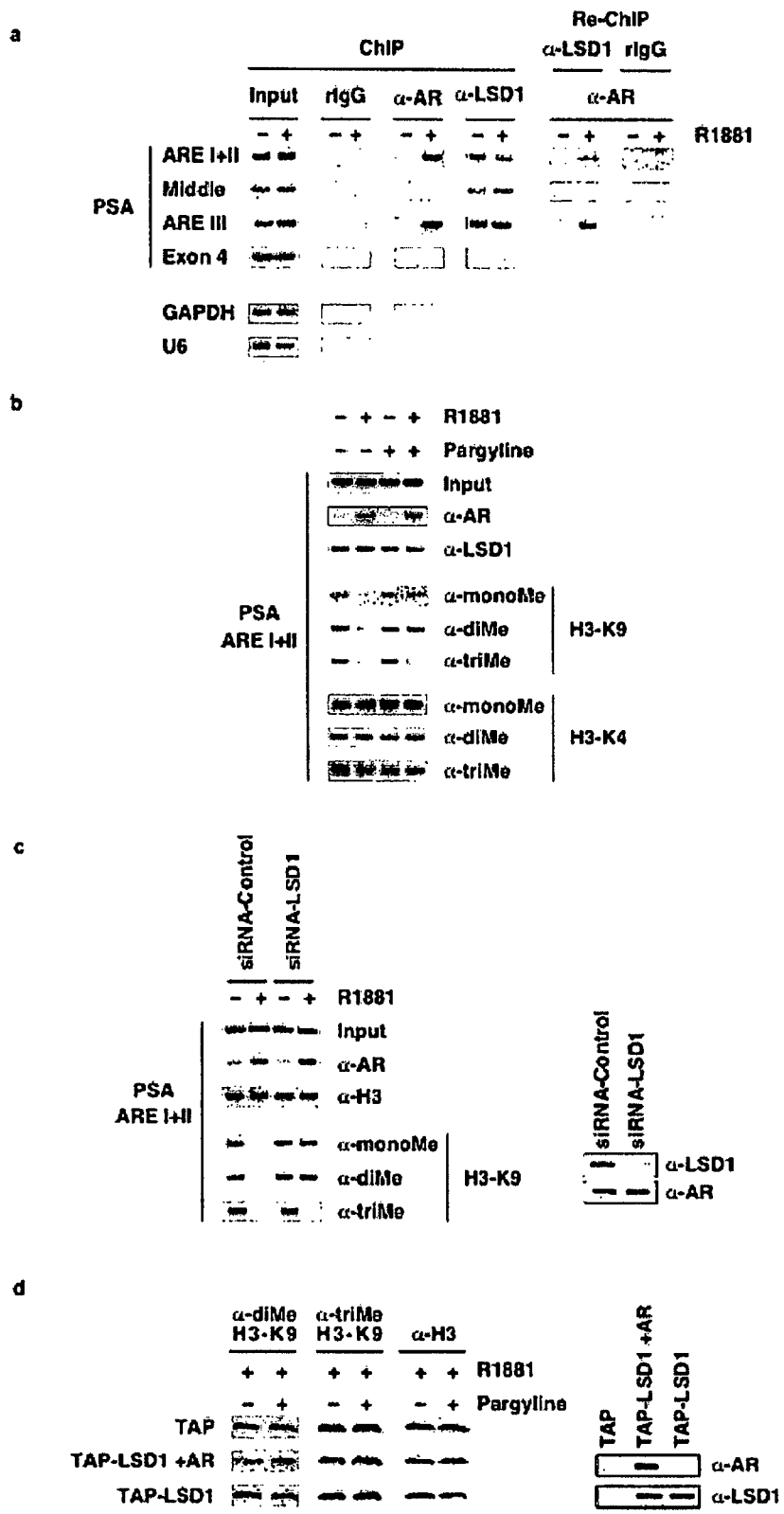
Figure 9:
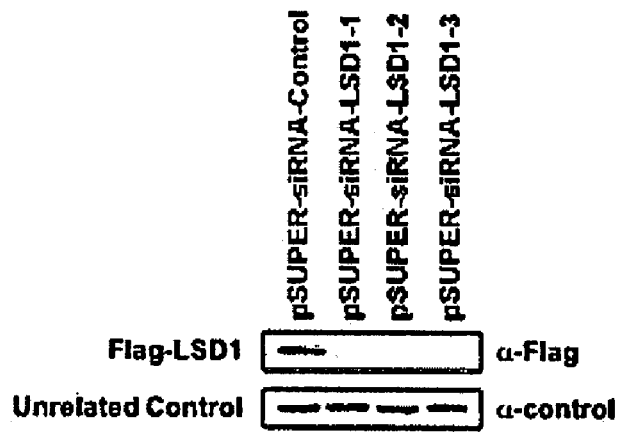

FIG. 9 shows siRNA mediated knockdown of LSD1. 293 cells were co-transfected with Flag-LSD1 and pSUPER constructs expressing siRNA against LSD1. The different DNA target sequences for siRNA are: LSD1-1 5'-CGGACAAGCT-GTTCCTAAA-3' (SEQ ID NO: 1); LSD1-2 5'-GAACTC-CATCAGCAATACA-3' (SEQ ID NO: 2); LSD1-3 5'-CA-CAAGGAAAGCTAGAAGA-3' (SEQ ID NO: 3); unrelated control 5'-CTTGCTATGAGAACAAATT-3' (SEQ ID NO: 10). 24 hours after transfection, cells were harvested and cell lysate was analysed in Western blot for expression of Flag-LSD1. The Western blot was decorated with an α-Flag antibody. The siRNA corresponding to LSD1-3 was used for the experiments in FIGS. 3 and 4.

Figure 10:
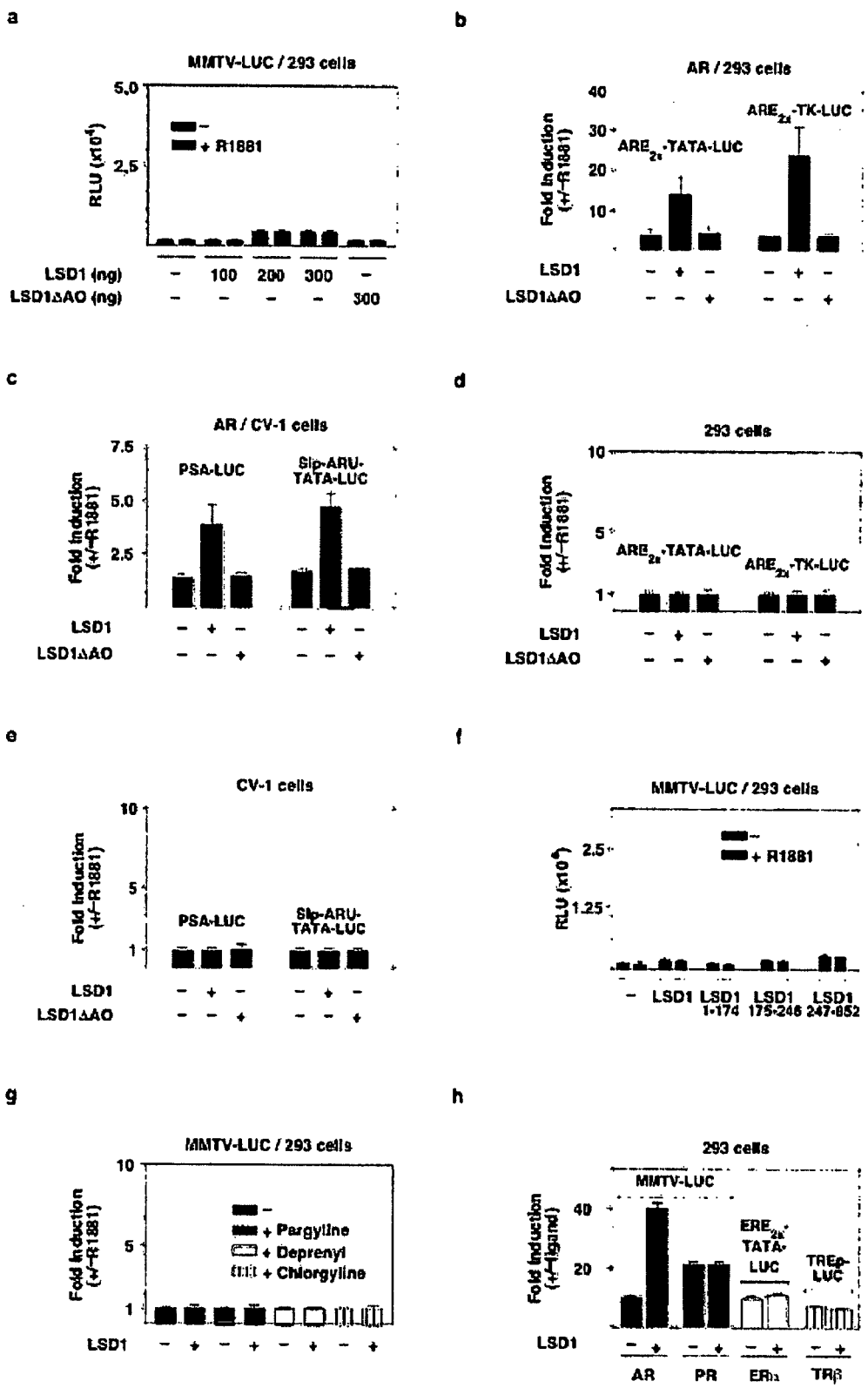
Figure 10:
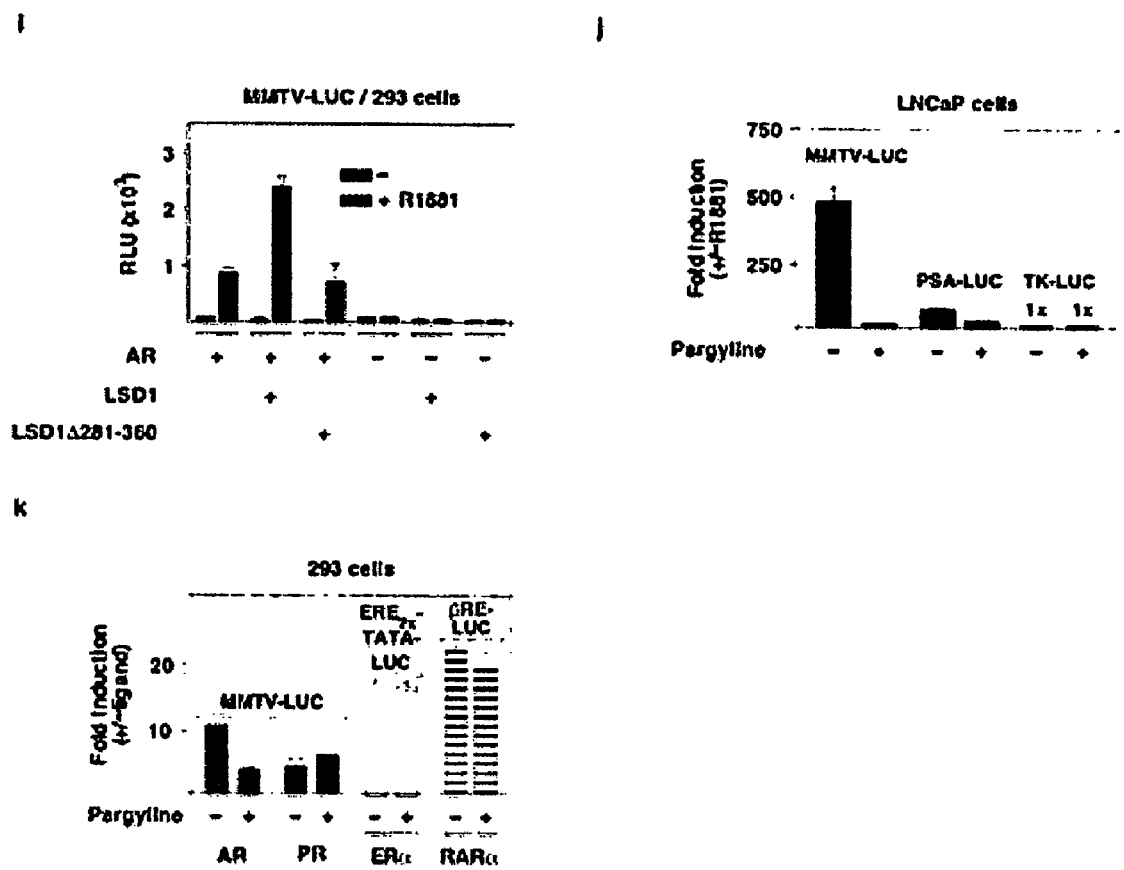

FIG. 10 shows the specificity of LSD1 in the control of AR-induced transcriptional activity. 293 (a, b, d, f, g, h, i, k), CV-1 (c, e), and LNCaP (j) cells were transfected with the indicated reporters in the absence of AR (a, d, e, f, g) or in presence of AR, PR, αRα, RARα, or TRα expression plasmids (b, c, h, i, k). Cells were treated with or without R1881, R5020, $E_2$, T3, all-trans RA, pargyline, deprenyl, and clorgyline. LSD1 induces ligand-dependent activation of AR reporters only in presence of AR (b, c) but not in absence of AR (a, d, e, f, g). LSD1 does not influence activation of other nuclear hormone receptors (h). The AO deletion mutant LSD1Δ281-360 fails to activate AR-dependent gene expression (i). Pargyline blocks AR-dependent reporter genes (j) but fails to block other nuclear hormone receptors (k). Bars represent mean ±SD (n>5).

The following detailed description of the invention refers to the invention in its broadest sense, but also to specific embodiments which may be preferred due to the excellent and surprising results achieved. However, the invention is by no means restricted to such preferred embodiments.

The invention relates to antibodies for use for modulating the activity of the lysine-specific demethylase (LSD1) in a mammal.

Furthermore, the invention also relates to antibodies for use for the manufacture of a diagnostic agent for modulating the activity of the lysine-specific demethylase (LSD1) in a mammal.

The specific target where the antibody or antibodies of the invention may be used is the prostate of a mammal, particularly the prostate of a human. The surprising finding on which the present invention is based is the fact that LSD1 is overexpressed in dedifferentiated and progressive prostate carcinomas, while it is not in prostate cells of less progressive stage carcinomas. When immunohistochemically staining prostate carcinoma tissue, prostate carcinoma cells, body fluids of (or containing) prostate carcinoma tissue and/or cells and/or protein extracts thereof, the staining intensity is a representative measure for the amount of LSD1 expressed which, in turn, is a good measure for the stage of carcinoma progression. In accordance with such a finding, anti-LSD1 antibodies are preferred for the practice of the invention.

In accordance with the invention, at least one anti-LSD1 antibody is used. There may be used one anti-LSD1 antibody or there may be used several anti-LSD1 antibodies. In preferred embodiments of the invention, the use comprises one anti-LSD1 antibody. Any anti-LSD1 antibody known to a skilled person may be employed in accordance with the present invention, which may be a monoclonal antibody or a polyclonal antibody. Antibodies of any known origin may be used, for example rabbit antibodies, mouse antibodies, to name only two examples. However, in preferred embodiments, the at least one anti-LSD1 antibody or the one anti-LSD1 antibody is selected from the group consisting of polyclonal or monoclonal antibodies matching with a certain epitope in the human LSD1 protein, particularly preferable the AGPGTAGGSENGSEVAAQPAGLSGPAE-VGPGAVGERTPRKKEPPRASPPGGLAEP-PGSAGPQAGPTVVPGSATPMETGIAET-PEGRRTSRRKRAKVEYREMDESLANLSEDEYYSE (SEQ ID NO: 4) epitope in the human LSD1 protein. In particularly preferred embodiments of the invention, the anti-LSD1 antibody used is selected from the following antibodies which are all matching with the above epitope of the human LSD1 protein: rabbit polyclonal anti-LSD1 antibody 5996, rabbit polyclonal anti-LSD1 antibody 5995, and mouse polyclonal anti-LSD1 antibody 5994. The rabbit polyclonal anti-LSD1 antibody 5996 is particularly preferred. The anti-LSD1 antibodies 5996, 5995 and 5994 are given by way of examples only, but the invention is not restricted to those antibodies.

In another aspect, the invention relates to a method for identifying and/or scoring prostate carcinomas, said method comprising the step of immunostaining tissues, cells, body fluids and/or protein extracts relating to prostate cancer including employing anti-LSD1 antibodies and quantifying the LSD1 amount in said tissues, cells, body fluids and/or protein extracts.

As was surprisingly found, the LSD1 overexpressed in prostate cancer tissue, prostate cancer cells, body fluids of (or containing) prostate cancer tissue and/or cells or protein extracts thereof is targeted by anti-LSD1 antibodies. As a result, the amount of LSD1 expressed in accordance with the severity of the carcinoma and targeted by the respective antibodies can be detected directly or indirectly in accordance with methods of detecting protein-antibody complexes usually applied in the art. In this connection, the term "directly" has the meaning a skilled person would attribute to the term usually, i.e. any method by which a direct detection of such a complex is possible. (Non-restricting) examples of such direct methods are methods by which the presence of a certain molecule (complex) in a substance mixture can be established, as, for example, spectrometric (optical spectometry, mass spectrometry, etc.) methods or chromatographic (HPLC, column chromatography, thin layer chromatography etc.) methods or combinations thereof. In contrast, the term "indirectly" means, in accordance with the usual definition of a skilled person, any method by which an indirect detection of such a complex is possible. (Non-restricting) examples of such indirect methods are methods by which another molecule or chemical entity, including an antibody, is added to the complex mixture upon which step the additional molecule, entity (including the antibody) binds to the complex, which binding results into a (qualitatively and quantitatively) sensitive detection of the presence of the LSD1-anti-LSD1 antibody complex. Exemplary methods comprise (but are not restricted to) direct or indirect immunohistochemistry, immunocytochemistry and ELISA technologies or combinations thereof.

As mentioned above, the method may be applied to all parts of the mammalian body where the LSD1 overexpression occurs and/or overexpressed LSD1 can be detected. Examples are prostate (cancer) tissues, prostate (cancer) cells, body fluids from such tissues or cells wherein LSD1 can be found as well as protein extracts thereof. Prostate cancer tissue is preferred in accordance with the invention at present, without that the invention is restricted to prostate cancer tissue. The tissue or cell or body fluid sample may be obtained from biopsy samples from mammalian (most preferably human) prostate cancer specimens or from surgical specimens of prostatectomies. The sample may be a tissue section or may be cells or cell combinations, while the body fluid may be a fluid obtained from prostate cancer tissue (of any origin) or from corresponding cells, for example blood or serum. In addition, the method may be applied to protein extracts obtained from such tissues and/or cells such extracts being prepared by means of using solvents or solvent mixtures compatible with the biological/medical object and with the detection method described herein.

In accordance with the method of the invention, at least one anti-LSD1 antibody is employed in the method. There may be employed one anti-LSD1 antibody or there may be employed several anti-LSD1 antibodies. In preferred embodiments of the invention, the method employs one anti-LSD1 antibody. Any anti-LSD1 antibody known to a skilled person may be employed in accordance with the method of the present invention, which antibody may be a monoclonal antibody or a polyclonal antibody. Antibodies of any known origin may be used, for example rabbit antibodies, mouse antibodies, to name only two examples. However, in preferred embodiments, the at least one anti-LSD1 antibody or the one anti-LSD1 antibody is selected from the group consisting of polyclonal or monoclonal antibodies matching with a certain epitope in the human LSD1 protein, particularly preferable the AGPGTAGGSENGSEVAAQPAGLSGPAE-VGPGAVGERTPRKKEPPRASPPGGLAEP-PGSAGPQAGPTVVPGSATPMETGIAET-PEGRRTSRRKRAKVEYREMDESLANLSEDEYYSE (SEQ ID NO: 4) epitope in the human LSD1 protein. In particularly preferred embodiments of the invention, the anti-LSD1 antibody used is selected from the following antibodies which are all matching with the above epitope of the human LSD1 protein: rabbit polyclonal anti-LSD1 antibody 5996, rabbit polyclonal anti-LSD1 antibody 5995, and mouse polyclonal anti-LSD1 antibody 5994. The rabbit polyclonal anti-LSD1 antibody 5996 is particularly preferred. The anti-LSD1 antibodies 5996, 5995 and 5994 are given by way of examples only, but the invention is not restricted to those antibodies.

In the method of the invention, the at least one anti-LSD1 antibody is applied to the tissue, cell(s), body fluid and/or protein extracts thereof. This can preferably be performed by steps known per se to a person having ordinary skill in this field. Once the antibody is combined with the respective other component(s) (i.e. the tissue, cell(s), body fluid(s) and/or protein extract(s) thereof), the detection step is performed, wherein either a direct or an indirect detection is selected from the methods described above. In one method presently preferred, another antibody is added to the LSD1-anti-LSD1 antibody complex which, again is specific enough, more preferably which is highly specific for the detection of the complex. By such a method, a highly specific detection of the LSD1 present in the tissue, cell(s), body fluid(s) and/or protein extracts thereof can be obtained. Said highly specific detection is the basis for the use of this method in the surprisingly specific discrimination of progressive or less progressive prostate carcinomas.

As an even more preferred embodiment, a typical immunohistochemical analysis can be performed, by a person having ordinary skill in this technical field[29], on tissue specimens or cells collected from prostate cancer tissues according to the following protocol: 5 µm tissue sections were cut from formalin-fixed paraffin-embedded specimens and treated in a microwave oven (6×4 min, 750 W, in 10 mM citrate buffer) for antigen retrieval. After incubation with the primary anti-LSD1 antibodies described above (1:500 overnight at 4° C.) the specific immunoreaction was detected using a secondary anti-rabbit IgG (1:500, commercially available from Dako, Copenhagen, Denmark) and visualized with the ABC complex (commercially available from Vector Laboratories Burlingame, Vt.) diluted in 1:50 phosphate buffered saline (PBS).

In another preferred embodiment of the invention, a direct detection of the LDS1-anti-LSD1-antibody with suitable means, more preferably spectroscopic means (e.g. (not restricting) mass spectrometry) or with chromatographic means (e.g. (not restricting) HPLC or thin layer chromatography) may be conducted. Also combinations of such procedures are suitable, as a skilled person will recognize.

In another aspect, the invention also relates to the use of at least one antibody for identifying and/or scoring prostate carcinomas in a mammal.

The invention also relates to the use of at least one antibody for the manufacture of a diagnostic agent for identifying and/or scoring prostate carcinomas in a mammal.

In accordance with the invention, at least one anti-LSD1 antibody is used. There may be used one anti-LSD1 antibody or there may be used several anti-LSD1 antibodies. In preferred embodiments of the invention, the use comprises one anti-LSD1 antibody. Any anti-LSD1 antibody known to a skilled person may be employed in accordance with the present invention, which may be a monoclonal antibody or a polyclonal antibody. Antibodies of any known origin may be used, for example rabbit antibodies, mouse antibodies, to name only two examples. However, in preferred embodiments, the at least one anti-LSD1 antibody or the one anti-LSD1 antibody is selected from the group consisting of polyclonal or monoclonal antibodies matching with a certain epitope in the human LSD1 protein, particularly preferable the AGPGTAGGSENGSEVAAQPAGLSGPAE-VGPGAVGERTPRKKEPPRASPPGGLAEP-PGSAGPQAGPTVVPGSATPMETGIAET-PEGRRTSRRKRAKVEYREMDESLANLSEDEYYSE (SEQ ID NO: 4) epitope in the human LSD1 protein. In particularly preferred embodiments of the invention, the anti- LSD1 antibody used is selected from the following antibodies which are all matching with the above epitope of the human LSD1 protein: rabbit polyclonal anti-LSD1 antibody 5996, rabbit polyclonal anti-LSD1 antibody 5995, and mouse polyclonal anti-LSD1 antibody 5994. The rabbit polyclonal anti-LSD1 antibody 5996 is particularly preferred. The anti-LSD1 antibodies 5996, 5995 and 5994 are given by way of examples only, but the invention is not restricted to those antibodies.

In accordance with the invention described above, the novel antibodies of the present invention may be used for modulating the activity of the lysine-specific demethylase (LSD1) in a mammal and for the manufacture of a medicament or diagnostic composition for modulating the activity of the lysine-specific demethylase (LSD1) in a mammal. Further areas for a diagnostic and therapeutic use of the antibodies of the present invention are in assays as for example Western blotting, immunohistochemistry, immunocytochemistry, enzyme-linked immunosorbent assay (ELISA), immunoprecipitation, Chromatin Immunoprecipitation (ChIP), screening of libraries, and flow cytometric analyses. In addition, antibodies are now being designed for therapeutic applications, including suppression of the immune system after organ transplantation, and for a treatment of cancers.

In another aspect, the invention relates to the use of at least one siRNA (short interfering RNA) for modulating the activity of the lysine-specific demethylase (LSD1) in a mammal.

In a further aspect, the invention relates to the use of at least one siRNA (short interfering RNA) for the manufacture of a medicament for modulating the activity of the lysine-specific demethylase (LSD1) in a mammal.

In accordance with the invention, at least one short interfering RNA (siRNA) is used. The siRNA must be capable to target LSD1 DNA sequences involved in the modulation of the activity of the lysine-specific demethylase (LSD1) in a mammal. There may be used one siRNA or there may be used several siRNAs. In preferred embodiments of the invention, the use comprises one siRNA. Any siRNA known to a skilled person may be employed in accordance with the present invention. However, in preferred embodiments, the at least one siRNA or the one siRNA is selected from the group consisting of siRNAs capable to target the following LSD1 DNA sequences LSD1-1 to LSD1-5 involved in the modulation of the activity of the lysine-specific demethylase (LSD1) in a mammal:

```
LSD1-1:  5'-AACGGACAAGCTGTTCCTAAA-3'    (SEQ ID NO: 11)

LSD1-2:  5'-AAGAACTCCATCAGCAATACA-3'   (SEQ ID NO: 12)

LSD1-3:  5'-AACACAAGGAAAGCTAGAAGA-3'   (SEQ ID NO: 13)

LSD1-4:  5'-AAGTGTCAATTTGTTCGGGCAT-3'  (SEQ ID NO: 14)

LSD1-5:  5'-AAGCGAGGCGAGGCAAGGCTT-3'.  (SEQ ID NO: 15)
```

In particularly preferred embodiments of the invention, the siRNAs used are the following, wherein S denotes the sense strand of the double-stranded siRNA and A denotes the anti-sense strand of the double-stranded siRNA:

```
siRNA-1:
S:  5'-CGGACAAGCUGUUCCUAAAUU-3'    (SEQ ID NO: 5)
A:  3'-UUGCCUGUUCGACAAGGAUUU-5'   (SEQ ID NO: 16)

siRNA-2:
S:  5'-GAACUCCAUCAGCAAUACAUU-3'    (SEQ ID NO: 6)
A:  3'-UUCUUGAGGUAGUCGUUAUGU-5'   (SEQ ID NO: 17)

siRNA-3:
S:  5'-CACAAGGAAAGCUAGAAGAUU-3'    (SEQ ID NO: 7)
A:  3'-UUGUGUUCCUUUCGAUCUUCU-5'   (SEQ ID NO: 18)

siRNA4:
S:  5'-GUGUCAAUUUGUUCGGGCAUUU-3'   (SEQ ID NO: 8)
A:  3'-UUCACAGUUAAACAAGCCCGUA-5'  (SEQ ID NO: 19)

siRNA-5:
S:  5'-GCGAGGCGAGGCAAGGCUUUU-3'    (SEQ ID NO: 9)
A:  3'-UUCGCUCCGCUCCGUUCCGAA-5'.  (SEQ ID NO: 20)
```

Another aspect of the invention relates to the use of at least one anti-LSD1 antibody for modulating the activity of the lysine-specific demethylase (LSD1) in a mammal.

In a further aspect, the invention also relates to the use of at least one anti-LSD1 antibody for the manufacture of a medicament for modulating the activity of the lysine-specific demethylase (LSD1) in a mammal.

In accordance with the invention, at least one anti-LSD1 antibody is used. There may be used one anti-LSD1 antibody or there may be used several anti-LSD1 antibodies. In preferred embodiments of the invention, the use comprises one anti-LSD1 antibody. Any anti-LSD1 antibody known to a skilled person may be employed in accordance with the present invention, which may be a monoclonal antibody or a polyclonal antibody. Antibodies of any known origin may be used, for example rabbit antibodies, mouse antibodies, to name only two examples. However, in preferred embodiments, the at least one anti-LSD1 antibody or the one anti-LSD1 antibody is selected from the group consisting of polyclonal or monoclonal antibodies matching with a certain epitope in the human LSD1 protein, particularly preferable the AGPGTAGGSENGSEVAAQPAGLSGPAE-VGPGAVGERTPRKKEPPRASPPGGLAEP-PGSAGPQAGPTVVPGSATPMETGIAET-PEGRRTSRRKRAKVEYREMDESLANLSEDEYYSE (SEQ ID NO: 4) epitope in the human LSD1 protein. In particularly preferred embodiments of the invention, the anti-LSD1 antibody used is selected from the following antibodies which are all matching with the above epitope of the human LSD1 protein: rabbit polyclonal anti-LSD1 antibody 5996, rabbit polyclonal anti-LSD1 antibody 5995, and mouse polyclonal anti-LSD1 antibody 5994. The rabbit polyclonal anti-LSD1 antibody 5996 is particularly preferred. The anti-LSD1 antibodies 5996, 5995 and 5994 are given by way of examples only, but the invention is not restricted to those antibodies.

In another aspect, the invention relates to the use of at least one siRNA in combination with at least one anti-LSD1 antibody for modulating the activity of the lysine-specific demethylase (LSD1) in a mammal.

In a further aspect, the invention also relates to the use of at least one siRNA in combination with at least one anti-LSD1 antibody for the manufacture of a medicament for modulating the activity of the lysine-specific demethylase (LSD1) in a mammal.

In accordance with the invention, at least one siRNA and at least one anti-LSD1 antibody is used. There may be used one siRNA in combination with one anti-LSD1 antibody, or there may be used one siRNA in combination with several anti-LSD1 antibodies, or there may be used several siRNAs in combination with one anti-LSD1 antibody, or there may be used several siRNAs in combination with several anti-LSD1 antibodies. In preferred embodiments of the invention, the use comprises one siRNA in combination with one anti-LSD1 antibody. Any siRNA in combination with any anti-LSD1 antibody known to a skilled person may be employed in accordance with the present invention. However, in particularly preferred embodiments, the at least one siRNA or the one siRNA is selected from the group consisting of those siRNAs capable to target the above-referenced LSD1 DNA sequences LSD1-1 to LSD1-5 involved in the modulation of the activity of the lysine-specific demethylase (LSD1) in a mammal, even more preferable to those siRNAs selected from the group consisting of the double-stranded siRNAs siRNA-1 to siRNA-5 mentioned above, and the at least one anti-LSD1 antibody or the one anti-LSD1 antibody is selected from the group consisting of those polyclonal or monoclonal antibodies matching with a certain epitope in the human LSD1 protein, particularly preferably the above-mentioned epitope of the human LSD1 protein. In even more preferred embodiments of the invention, the anti-LSD1 antibody used is the rabbit polyclonal anti-LSD1 antibody 5996, the rabbit polyclonal anti-LSD1 antibody 5995, or the mouse polyclonal anti-LSD1 antibody 5994.

According to another aspect, the invention relates to the use of at least one siRNA or to the use of at least one anti-LSD1 antibody or to the use of at least one siRNA in combination with at least one anti-LSD1 antibody, wherein any of those components, or the combination thereof, is used in combination with at least one amine oxidase inhibitor, all those uses being for modulating the activity of the lysine-specific demethylase (LSD1) in a mammal. In other words: The uses according to this aspect of the invention comprise the use of at least one siRNA in combination with at least one amine oxidase inhibitor; or at least one anti-LSD1 antibody in combination with at least one amine oxidase inhibitor; or at least one siRNA in combination with at least one anti-LSD1 antibody and in combination with at least one amine oxidase inhibitor.

In accordance with the invention, at least one amine oxidase inhibitor is used in any of the above combinations. There may be used one amine oxidase inhibitor or there may be used several amine oxidase inhibitors in the above combinations. In preferred embodiments of the invention, the use with view to the above combinations comprises one amine oxidase inhibitor. Any amine oxidase inhibitor may be employed for the combined uses in accordance with the present invention. However, in preferred embodiments, the at least one amine oxidase inhibitor or the one amine oxidase inhibitor in those combinations is selected from the group of the monoamine oxidase inhibitors (MAOIs) comprising both monoamine oxidase A and monoamine oxydase B (MAO-A and MAO-B) inhibitors. These compounds can be nardil (phenelzine sulfate), phenelzin, parnate (tranylcypromine sulfate), tranylcypromine, isocarbazid, selegiline, deprenyl, clorgyline, pargyline, furazolidon, marplan (isocarboxazid), l-deprenyl (Eldepryl), moclobemide (Aurorex or Manerix), furazolidone, harmine, harmaline, tetrahydroharmine, nialamide, or any extract from plant, insect, fish, mammals that contains MAOIs. Even more preferably, the at least one amine oxidase inhibitor in the above combinations is selected from pargyline, clorgyline and deprenyl. Advantageously and, hence, most preferred, the amine oxidase inhibitor in the above combinations is pargyline.

According to the present invention, the at least one siRNA and/or the at least one anti-LSD1 antibody and/or the at least one amine oxidase inhibitor in the above aspects is/are used, for example is/are used for the manufacture of a medicament, for modulating the activity of the lysine-specific demethylase, which is usually abbreviated as "LSD1". The term "modulating", as used in the present specification and claims, means a change either in the direction of improving the activity or in the direction of reducing the activity; in accordance with the present invention, a blocking of the LDS1 activity is preferred.

In a preferred embodiment of the inventive uses, the activity of LSD1 modulated is the LSD1 demethylating activity. This means that the LSD1 exerts an influence as a catalyst in a chemical reaction where target methyl groups in a polymer molecule are removed, and thereby any influence on the molecule's activity is effected. To give just one example, an amine oxidase inhibitor used in accordance with a preferred embodiment of the invention may block demethylation of mono- and dimethyl H3-K9 during androgen-induced transcription. In a further preferred embodiment of the invention, when using at least one amine oxidase inhibitor, the demethylase activity of LSD1 controlled is the demethylating action of LSD1 on repressing histone marks on the histone H3 and/or the histone H4, preferably on repressing histone marks on the lysine residue 9 on the histone H3 (H3-K9), and/or the lysine residue 20 on the histone H4 (H4-K20), more preferably on the repressing histone marks on mono- and dimethyl H3-K9 and/or H4-K20, thereby increasing AR regulated gene expression.

In another preferred embodiment of the invention, the mammal in connection to which the amine oxidase inhibitors are used is a human. Even more preferred, when applying the invention to a human, the LSD1 demethylase activity is targeted to tissues where the AR plays a pivotal physiological role, preferably wherein the LSD1 demethylase activity is targeted to the brain, testis or prostate of a human, and/or any other tissue where both LSD1 and AR are co-expressed and co-localize.

According to another aspect, the invention relates to a pharmaceutical composition for controlling the androgen receptor-dependent gene expression, said composition comprising an effective dose of at least one siRNA suitable for modulating the activity of the lysine-specific demethylase (LSD1) in a mammal.

According to a further aspect, the invention relates to a pharmaceutical composition for controlling the androgen receptor-dependent gene expression, said composition comprising an effective dose of at least one anti-LSD1 antibody suitable for modulating the activity of the lysine-specific demethylase (LSD1) in a mammal.

In another aspect, the invention relates to a pharmaceutical composition for controlling the androgen receptor-dependent gene expression, said composition comprising an effective dose of at least one siRNA in combination with at least one anti-LSD1 antibody suitable for modulating the activity of the lysine-specific demethylase (LSD1) in a mammal.

In another aspect, the invention relates to a pharmaceutical composition for controlling the androgen receptor-dependent gene expression, said composition comprising an effective dose of at least one siRNA and/or at least one anti-LSD1 antibody, any or both of them in combination with at least one amine oxidase inhibitor suitable for modulating the activity of the lysine-specific demethylase (LSD1) in a mammal.

In accordance with the invention, it is particularly preferred that the activity of LSD1 modulated by applying the at least one siRNA and/or the at least one anti-LSD1 antibody, optionally any of them or both of them in combination with at least one amine oxidase inhibitor, is the demethylating activity of LSD1.

In accordance with the invention, the pharmaceutical composition comprises at least one siRNA. The siRNA must be capable to target LSD1 DNA sequences involved in the modulation of the activity of the lysine-specific demethylase (LSD1) in a mammal. There may be comprised one siRNA, or there may be comprised several siRNAs. In preferred embodiments of the invention, the pharmaceutical composition comprises one siRNA. Any siRNA known to a skilled person may be comprised in the pharmaceutical composition of the present invention. However, in preferred embodiments, the at least one siRNA or the one siRNA which is comprised by the pharmaceutical composition of the invention is selected from the group consisting of siRNAs capable to target the following LSD1 DNA sequences LSD1-1 to LSD1-5 involved in the modulation of the activity of the lysine-specific demethylase (LSD1) in a mammal:

```
LSD1-1:  5'-AACGGACAAGCTGTTCCTAAA-3'   (SEQ ID NO: 11)

LSD1-2:  5'-AAGAACTCCATCAGCAATACA-3'   (SEQ ID NO: 12)

LSD1-3:  5'-AACACAAGGAAAGCTAGAAGA-3'   (SEQ ID NO: 13)

LSD1-4:  5'-AAGTGTCAATTTGTTCGGGCAT-3'  (SEQ ID NO: 14)

LSD1-5:  5'-AAGCGAGGCGAGGCAAGGCTT-3'.  (SEQ ID NO: 15)
```

In particularly preferred embodiments of the invention, the siRNAs comprised in the pharmaceutical composition are the following, wherein S denotes the sense strand of the double-stranded siRNA and A denotes the antisense strand of the double-stranded siRNA:

```
siRNA-1:
S:  5'-CGGACAAGCUGUUCCUAAAUU-3'   (SEQ ID NO: 5)
A:  3'-UUGCCUGUUCGACAAGGAUUU-5'   (SEQ ID NO: 16)

siRNA-2:
S:  5'-GAACUCCAUCAGCAAUACAUU-3'   (SEQ ID NO: 6)
A:  3'-UUCUUGAGGUAGUCGUUAUGU-5'   (SEQ ID NO: 17)

siRNA-3:
S:  5'-CACAAGGAAAGCUAGAAGAUU-3'   (SEQ ID NO: 7)
A:  3'-UUGUGUUCCUUUCGAUCUUCU-5'   (SEQ ID NO: 18)

siRNA4:
S:  5'-GUGUCAAUUUGUUCGGGCAUUU-3'  (SEQ ID NO: 8)
A:  3'-UUCACAGUUAAACAAGCCCGUA-5'  (SEQ ID NO: 19)

siRNA-5:
S:  5'-GCGAGGCGAGGCAAGGCUUUU-3'   (SEQ ID NO: 9)
A:  3'-UUCGCUCCGCUCCGUUCCGAA-5'.  (SEQ ID NO: 20)
```

In accordance with other embodiments of the present invention, the pharmaceutical composition comprises at least one anti-LSD1 antibody. The pharmaceutical composition may comprise one anti-LSD1 antibody or may comprise several anti-LSD1 antibodies. In preferred embodiments of the invention, the pharmaceutical composition comprises one anti-LSD1 antibody. Any anti-LSD1 antibody known to a skilled person may be comprised in the pharmaceutical composition of the present invention, which may be a monoclonal antibody or a polyclonal antibody. Antibodies of any known origin may be included into the pharmaceutical composition, for example rabbit antibodies, mouse antibodies, to name only two examples. However, in preferred embodiments, the at least one anti-LSD1 antibody or the one anti-LSD1 antibody comprised by the pharmaceutical composition is selected from the group consisting of polyclonal or monoclonal antibodies matching with a certain epitope in the human LSD1 protein, particularly preferable the AGPGTAGGSENGSEVAAQPAGLSGPAEVGP-GAVGERTPRKKEPPRASPPGGLAEPPG-SAGPQAGPTVVPGSATPMETGIAETPEGRRTSRRKRA KVEYREMDESLANLSEDEYYSE (SEQ ID NO: 4) epitope in the human LSD1 protein. In particularly preferred embodiments of the invention, the anti-LSD1 antibody included into the pharmaceutical composition is selected from the following antibodies which are all matching with the above epitope of the human LSD1 protein: rabbit polyclonal anti-LSD1 antibody 5996, rabbit polyclonal anti-LSD1 antibody 5995, and mouse polyclonal anti-LSD1 antibody 5994. The rabbit polyclonal anti-LSD1 antibody 5996 is particularly preferably included into the pharmaceutical compositions of the invention.

Further embodiments of the invention are directed to pharmaceutical compositions which comprise at least one siRNA in combination with at least one anti-LSD1 antibody. The pharmaceutical composition of the invention may comprise one siRNA in combination with one anti-LSD1 antibody, or it may comprise one siRNA in combination with several anti-LSD1 antibodies, or it may comprise several siRNAs in combination with one anti-LSD1 antibody, or it may comprise several siRNAs in combination with several anti-LSD1 antibodies. In preferred embodiments of the invention, the pharmaceutical composition of the invention comprises one siRNA in combination with one anti-LSD1 antibody. Any siRNA in combination with any anti-LSD1 antibody known to a skilled person may be employed in accordance with the present invention. However, in particularly preferred embodiments, the at least one siRNA or the one siRNA comprised in the pharmaceutical composition is selected from the group consisting of those siRNAs capable to target the above-referenced LSD1 DNA sequences LSD1-1 to LSD1-5 involved in the modulation of the activity of the lysine-specific demethylase (LSD1) in a mammal, even more preferable to those siRNAs selected from the group consisting of the double-stranded siRNAs siRNA-1 to siRNA-5 mentioned above, and the at least one anti-LSD1 antibody or the one anti-LSD1 antibody comprised in the pharmaceutical composition is selected from the group consisting of those polyclonal or monoclonal antibodies matching with a certain epitope in the human LSD1 protein, particularly preferably the above-mentioned epitope of the human LSD1 protein. In even more preferred embodiments of the invention, the anti-LSD1 antibody used is the rabbit polyclonal anti-LSD1 antibody 5996, the rabbit polyclonal anti-LSD1 antibody 5995, or the mouse polyclonal anti-LSD1 antibody 5994.

In further embodiments, the pharmaceutical composition of the invention comprises at least one siRNA or comprises at least one anti-LSD1 antibody or comprises at least one siRNA in combination with at least one anti-LSD1 antibody, wherein any of those components, or the combination thereof, is present in the pharmaceutical composition of the invention in combination with at least one amine oxidase inhibitor. In other words: The pharmaceutical compositions according to this aspect of the invention comprise at least one siRNA in combination with at least one amine oxidase inhibitor; or at least one anti-LSD1 antibody in combination with at least one amine oxidase inhibitor; or at least one siRNA in combination with at least one anti-LSD1 antibody and in combination with at least one amine oxidase inhibitor.

In a preferred pharmaceutical composition according to the invention, one amine oxidase inhibitor is used, although the use of more than one amine oxidase inhibitor is possible and may be advantageous. In even more preferred embodiments, the pharmaceutical compositions comprise at least one, particularly preferred exactly one amine oxidase inhibitor selected from the group of the monoamine oxidase inhibitors (MAOIs) comprising both monoamine oxidase A and monoamine oxydase B (MAO-A and MAO-B) inhibitors.

These compounds can be nardil (pheneizine sulfate), phenelzin, parnate (tranylcypromine sulfate), tranylcypromine, isocarbazid, selegiline, deprenyl, clorgyline, pargyline, furazolidon, marplan (isocarboxazid), I-deprenyl (Eldepryl), moclobemide (Aurorex or Manerix), furazolidone, harmine, harmaline, tetrahydroharmine, nialamide, or any extract from plant, insect, fish, mammals that contains MAOIs, preferably wherein the amine oxidase inhibitors are selected from pargyline, clorgyline and deprenyl, more preferably wherein the amine oxidase inhibitor is pargyline.

It goes without saying that preferred pharmaceutical compositions according to the invention, in addition to the siRNA and/or the anti-LSD1 antibody and/or the amine oxidase inhibitor, may contain further components which a skilled person may select in accordance with his ordinary skill. Those components may comprise solvents, carriers, excipients, auxiliary substances by which particular properties of the composition may be established and/or adjusted; such substances may exert an own effect or may contribute to contribute to effects exerted by other components. Examples of such additional substances can be selected by a person having ordinary skill in this technical field in accordance with the requirements, are well known and, hence, need no further detailed description here.

The invention, in another aspect, also relates to a method for controlling the androgen receptor-dependent gene expression in a mammal, said process comprising the step of administering to said mammal, on a suitable route, an effective dose of a pharmaceutical composition modulating an activity of the lysine-specific demethylase (LSD1) in a mammal.

In the method of the invention, it is preferred that the activity of LSD1 modulated is the LSD1 demethylating activity.

In preferred embodiments of the method, the modulation is effected by means of at least one siRNA. The siRNA must be capable to target LSD1 DNA sequences involved in the modulation of the activity of the lysine-specific demethylase (LSD1) in a mammal. In a preferred method according to the invention, one siRNA is used, although the use of more than one siRNA is possible and may be advantageous. In even more preferred embodiments, the method comprises the application or administration of at least one, particularly preferred exactly one siRNA selected from the group consisting of siRNAs capable to target the following LSD1 DNA sequences LSD1-1 to LSD1-5 involved in the modulation of the activity of the lysine-specific demethylase (LSD1) in a mammal:

```
LSD1-1:  5'-AACGGACAAGCTGTTCCTAAA-3'   (SEQ ID NO: 11)
LSD1-2:  5'-AAGAACTCCATCAGCAATACA-3'   (SEQ ID NO: 12)
LSD1-3:  5'-AACACAAGGAAAGCTAGAAGA-3'   (SEQ ID NO: 13)
LSD1-4:  5'-AAGTGTCAATTTGTTCGGGCAT-3'  (SEQ ID NO: 14)
LSD1-5:  5'-AAGCGAGGCGAGGCAAGGCTT-3'.  (SEQ ID NO: 15)
```

In particularly preferred embodiments of the invention, the siRNAs used in the method are the following, wherein S denotes the sense strand of the double-stranded siRNA and A denotes the antisense strand of the double-stranded siRNA:

```
siRNA-1:
S: 5'-CGGACAAGCUGUUCCUAAAUU-3'    (SEQ ID NO: 5)
A: 3'-UUGCCUGUUCGACAAGGAUUU-5'    (SEQ ID NO: 16)

siRNA-2:
S: 5'-GAACUCCAUCAGCAAUACAUU-3'    (SEQ ID NO: 6)
A: 3'-UUCUUGAGGUAGUCGUUAUGU-5'    (SEQ ID NO: 17)
```

```
-continued
siRNA-3:
S: 5'-CACAAGGAAAGCUAGAAGAUU-3'    (SEQ ID NO: 7)
A: 3'-UUGUGUUCCUUUCGAUCUUCU-5'    (SEQ ID NO: 18)

siRNA4:
S: 5'-GUGUCAAUUUGUUCGGGCAUUU-3'   (SEQ ID NO: 8)
A: 3'-UUCACAGUUAAACAAGCCCGUA-5'   (SEQ ID NO: 19)

siRNA-5:
S: 5'-GCGAGGCGAGGCAAGGCUUUU-3'    (SEQ ID NO: 9)
A: 3'-UUCGCUCCGCUCCGUUCCGAA-5'.   (SEQ ID NO: 20)
```

In further preferred embodiments of the method, the modulation is effected by means of at least one anti-LSD1 antibody. In a preferred method according to the invention, one anti-LSD1 antibody is used, although the use of more than one anti-LSD1 antibody is possible and may be advantageous. Any anti-LSD1 antibody known to a skilled person may be employed in the method of the present invention, which may be a monoclonal antibody or a polyclonal antibody. Antibodies of any known origin may be used, for example rabbit antibodies, mouse antibodies, to name only two examples. In even more preferred embodiments, the method comprises the application or administration of at least one, particularly preferred exactly one anti-LSD1 antibody selected from the group consisting of polyclonal or monoclonal antibodies matching with a certain epitope in the human LSD1 protein, particularly preferable the AGPGTAGGSENGSEVAAQPA-GLSGPAEVGPGAVGERTPRKKEPPRASP-PGGLAEPPGSAGPQAGPTVVPGSATP-METGIAETPEGRRTSRRKRAKVEYREMDESLANLSE DEYYSE (SEQ ID NO: 4) epitope in the human LSD1 protein. In particularly preferred embodiments of the method of the invention, the anti-LSD1 antibody used is selected from the following antibodies which are all matching with the above epitope of the human LSD1 protein: rabbit polyclonal anti-LSD1 antibody 5996, rabbit polyclonal anti-LSD1 antibody 5995, and mouse polyclonal anti-LSD1 antibody 5994. The rabbit polyclonal anti-LSD1 antibody 5996 is particularly preferred.

Other preferred embodiments of the invention are directed to a method wherein the modulation is effected by means of at least one siRNA in combination with at least one anti-LSD1 antibody. In a preferred method according to the invention, one siRNA is used in combination with one anti-LSD1 antibody, although the use of more than one siRNA in combination with one anti-LSD1 antibody or the use of one siRNA in combination with more than one anti-LSD1 antibody or the use of more than one siRNA in combination with more than one anti-LSD1 antibody is possible and may be advantageous. In even more preferred embodiments, the method comprises the application or administration of at least one, particularly preferred exactly one siRNA selected from the group consisting of those siRNAs capable to target the above-referenced LSD1 DNA sequences LSD1-1 to LSD1-5 involved in the modulation of the activity of the lysine-specific demethylase (LSD1) in a mammal, even more preferable to those siRNAs selected from the group consisting of the double-stranded siRNAs siRNA-1 to siRNA-5 mentioned above, while the method employing the siRNA-3

```
siRNA-3:
S: 5'-CACAAGGAAAGCUAGAAGAUU-3'    (SEQ ID NO: 7)
A: 3'-UUGUGUUCCUUUCGAUCUUCU-5'    (SEQ ID NO: 18)
``` as the siRNA is preferred most, and the at least one anti-LSD1 antibody or the one anti-LSD1 antibody used in the method of the invention is selected from the group consisting of those polyclonal or monoclonal antibodies matching with a certain epitope in the human LSD1 protein, particularly preferably the above-mentioned epitope of the human LSD1 protein. In even more preferred embodiments of the invention, the anti-LSD1 antibody used in the method of the invention is the rabbit polyclonal anti-LSD1 antibody 5996, the rabbit polyclonal anti-LSD1 antibody 5995, or the mouse polyclonal anti-LSD1 antibody 5994, and the rabbit polyclonal anti-LSD1 antibody 5996 is preferred most.

In other preferred embodiments of the method, the modulation is effected by means of a combination of at least two of the group selected from at least one siRNA and at least one anti-LSD1 antibody and at least one amine oxidase inhibitor. In a particularly preferred modulation method, all three components (siRNA, anti-LSD1 antibody and amine oxidase inhibitor) may be used advantageously. In particularly preferred methods of the invention, a modulation of the activity of the lysine-specific demethylase (LSD1) in a mammal is effected by a combination of one siRNA and/or one anti-LSD1 antibody and/or one amine oxidase inhibitor, although more than one of either of them or more than one of all of them (siRNA, anti-LSD1 antibody and amine oxidase inhibitor) can be used in combination in the method of the invention and may be advantageous.

In even more preferred embodiments of the method of the invention, a combination is used which comprises one siRNA selected from the group consisting of those siRNAs capable to target the above-referenced LSD1 DNA sequences LSD1-1 to LSD1-5 involved in the modulation of the activity of the lysine-specific demethylase (LSD1) in a mammal, even more preferable to those siRNAs selected from the group consisting of the double-stranded siRNAs siRNA-1 to siRNA-5 mentioned above, or a combination which comprises one anti-LSD1 antibody selected from the group consisting of those polyclonal or monoclonal antibodies matching with a certain epitope in the human LSD1 protein, particularly preferably the above-mentioned epitope of the human LSD1 protein, and in even more preferred embodiments of the invention, the anti-LSD1 antibody used is the rabbit polyclonal anti-LSD1 antibody 5996, the rabbit polyclonal anti-LSD1 antibody 5995, or the mouse polyclonal anti-LSD1 antibody 5994, or a combination which comprises one amine oxidase inhibitor selected from the group of the monoamine oxidase inhibitors (MAOIs) comprising both monoamine oxidase A and monoamine oxydase B (MAO-A and MAO-B) inhibitors. These compounds can most preferably be nardil (phenelzine sulfate), phenelzin, parnate (tranylcypromine sulfate), tranylcypromine, isocarbazid, selegiline, deprenyl, clorgyline, pargyline, furazolidon, marplan (isocarboxazid), I-deprenyl (Eldepryl), moclobemide (Aurorex or Manerix), furazolidone, harmine, harmaline, tetrahydroharmine, nialamide, or any extract from plant, insect, fish, mammals that contains MAOIs, may, with utmost preference, be selected from pargyline, clorgyline and deprenyl, and most advantageously, the amine oxidase inhibitor in such combinations for the method of the invention is pargyline.

Particularly preferred embodiments of the method of the invention are characterized by that the demethylase activity of LSD1 controlled is the demethylating action of LSD1 on repressing histone marks on the histone H3 and/or the histone H4, preferably on repressing histone marks on the lysine residue 9 on the histone H3 (H3-K9), and/or the lysine residue 20 on the histone H4 (H4-K20), more preferably on the repressing histone marks on mono- and dimethyl H3-K9 and/or H4-K20, thereby increasing AR regulated gene expression.

The routes on which the administration of the effective dose of the pharmaceutical composition according to the invention to said mammal can be performed, can be any route of administration conceivable. The administration route may be selected by a skilled person in accordance with his ordinary skill and the requirements of the case. Just to mention few examples, the routes may be the oral, buccal, pulmonal, nasal, transdermal, intravenous, subcutaneous, intracutaneous, intramuscular, rectal, vaginal or intrathecal administration routes, optionally together with per se known carriers, adjuvants and additives. The oral, intravenous, subcutaneous or intracutaneous administration routes are preferred.

With respect to the targets concerned, the LSD1 demethylase activity may be directed to any target in a mammalian body, particularly in a human body. Preferably, the LSD1 demethylase activity is targeted to tissues where the AR plays a pivotal physiological role, preferably wherein the LSD1 demethylase activity is targeted to the brain, testis or prostate of a mammal, preferably of a human.

The invention also relates to a short interfering RNA ("siRNA") capable to target LSD1 DNA sequences involved in the modulation of the activity of the lysine-specific demethylase (LSD1) in a mammal. By combining any of the inventive siRNAs with the LSD1 DNA, a modulation of the activity and, in preferred cases of the invention, a down-regulation of the LSD1 demethylating activity, can be achieved. In preferred embodiments of the invention, those siRNAs are selected which are capable of targeting the following LSD1 DNA sequences LSD1-1 to LSD1-5 involved in the modulation of the activity of the lysine-specific demethylase (LSD1) in a mammal, particularly in a human:

```
LSD1-1: 5'-AACGGACAAGCTGTTCCTAAA-3'   (SEQ ID NO: 11)
LSD1-2: 5'-AAGAACTCCATCAGCAATACA-3'   (SEQ ID NO: 12)
LSD1-3: 5'-AACACAAGGAAAGCTAGAAGA-3'   (SEQ ID NO: 13)
LSD1-4: 5'-AAGTGTCAATTTGTTCGGGCAT-3'  (SEQ ID NO: 14)
LSD1-5: 5'-AAGCGAGGCGAGGCAAGGCTT-3'.  (SEQ ID NO: 15)
```

In particularly preferred embodiments, the invention is directed to the following siRNAs, wherein S denotes the sense strand of the double-stranded siRNA and A denotes the antisense strand of the double-stranded siRNA:

```
siRNA-1:
S: 5'-CGGACAAGCUGUUCCUAAAUU-3'        (SEQ ID NO: 5)
A: 3'-UUGCCUGUUCGACAAGGAUUU-5'        (SEQ ID NO: 16)

siRNA-2:
S: 5'-GAACUCCAUCAGCAAUACAUU-3'        (SEQ ID NO: 6)
A: 3'-UUCUUGAGGUAGUCGUUAUGU-5'        (SEQ ID NO: 17)

siRNA-3:
S: 5'-CACAAGGAAAGCUAGAAGAUU-3'        (SEQ ID NO: 7)
A: 3'-UUGUGUUCCUUUCGAUCUUCU-5'        (SEQ ID NO: 18)

siRNA4:
S: 5'-GUGUCAAUUUGUUCGGGCAUUU-3'       (SEQ ID NO: 8)
A: 3'-UUCACAGUUAAACAAGCCCGUA-5'       (SEQ ID NO: 19)

siRNA-5:
S: 5'-GCGAGGCGAGGCAAGGCUUU-3'         (SEQ ID NO: 9)
A: 3'-UUCGCUCCGCUCCGUUCCGAA-5'.       (SEQ ID NO: 20)
```

The invention is also directed to an anti-LSD1 antibody capable to target an epitope in the LSD1 protein of a mammal. By combining any of the inventive anti-LSD1 antibodies with certain epitopes of the LSD1 protein of a mammal, preferably of a human, a modulation of the activity and, in certain cases a down-regulation of the LSD1 demethylating activity, can be achieved. The invention is directed to monoclonal antibodies and to polyclonal antibodies. The antibodies may be of any origin and, hence, may be, for example (without restriction) rabbit antibodies, mouse antibodies etc. In preferred embodiments of the invention, those anti-LSD1 antibodies are selected which are matching with a certain epitope of the human LSD1 protein, particularly preferable with the AGPG-TAGGSENGSEVAAQPAGLSGPAEVGP-GAVGERTPRKKEPPRASPPGGLAEPPG-SAGPQAGPTVVPGSATPMETGIAETPEGRRTSRRKRA KVE[[RY]]YREMDESLANLSEDEYYSE (SEQ ID NO: 4) epitope in the human LSD1 protein. In particularly preferred embodiments of the invention, the anti-LSD1 antibody is selected from the following antibodies which are all matching with the above epitope of the human LSD1 protein: rabbit polyclonal anti-LSD1 antibody 5996, rabbit polyclonal anti-LSD1 antibody 5995, and mouse polyclonal anti-LSD1 antibody 5994. The rabbit polyclonal anti-LSD1 antibody 5996 is particularly preferred. The anti-LSD1 antibodies 5996, 5995 and 5994 are by way of example only, but the invention is not restricted to those antibodies.

In accordance with the invention described above, the novel siRNAs of the present invention may be used for modulating the activity of the lysine-specific demethylase (LSD1) in a mammal and for the manufacture of a medicament for modulating the activity of the lysine-specific demethylase (LSD1) in a mammal. Further areas for a diagnostic and therapeutic use of the siRNAs of the present invention are in assays effecting a combination of cell array and RNAi for high-throughput loss-of-function studies, in medicaments for an in vivo therapeutic application including treatment of cancers, using synthetic siRNA for target-specific gene silencing in vivo, in animal models and in RNAi-based therapeutics.

In accordance with the invention described above and as claimed in claims X to X, the novel antibodies of the present invention may be used for modulating the activity of the lysine-specific demethylase (LSD1) in a mammal and for the manufacture of a medicament for modulating the activity of the lysine-specific demethylase (LSD1) in a mammal. Further areas for a diagnostic and therapeutic use of the antibodies of the present invention are in assays as for example Western blotting, immunohistochemistry, immunocytochemistry, enzyme-linked immunosorbent assay (ELISA), immunoprecipitation, Chromatin Immunoprecipitation (ChIP), screening of libraries, and flow cytometric analyses. In addition, antibodies are now being designed for therapeutic applications, including suppression of the immune system after organ transplantation, and for a treatment of cancers.

The invention is described in more detail below, without restricting it to those embodiments specifically addressed in the above description as well as in the subsequent description of preferred embodiments.

Figure 2:
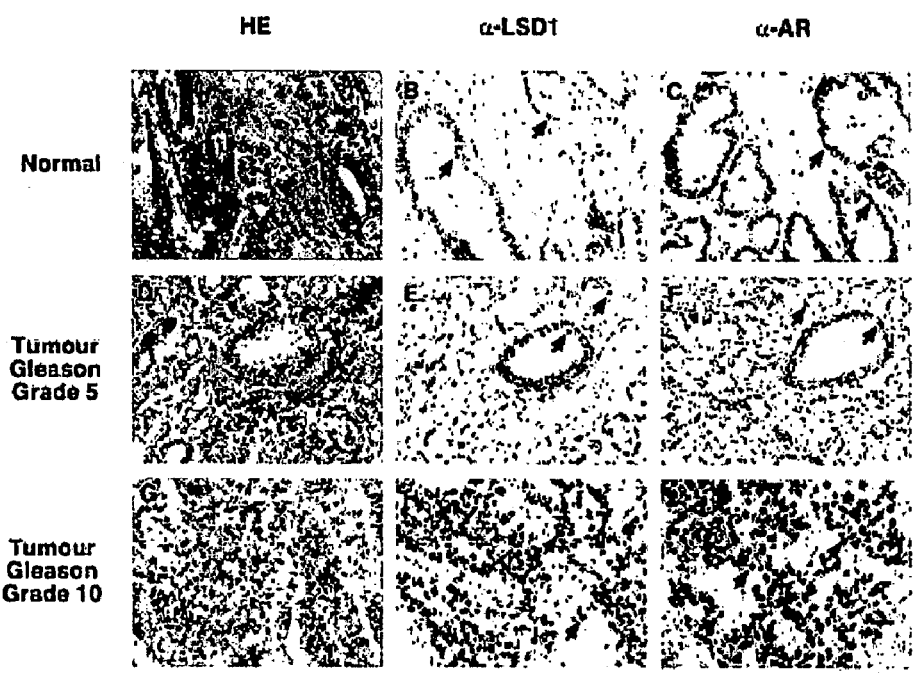
Figure 6:
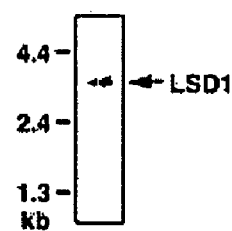
FIG. 6 shows LSD1 expression analyses. a, Expression of LSD1 in human tissues was examined by Northern blot analyses of human testis mRNA. b, Confocal laser scanning images shows sub-cellular localisation of endogenous LSD1 and AR in human LNCaP prostate tumour cells. AR (red) co-localises with LSD1 (green) in the nucleus upon addition of the AR agonist R1881.
Figure 6:
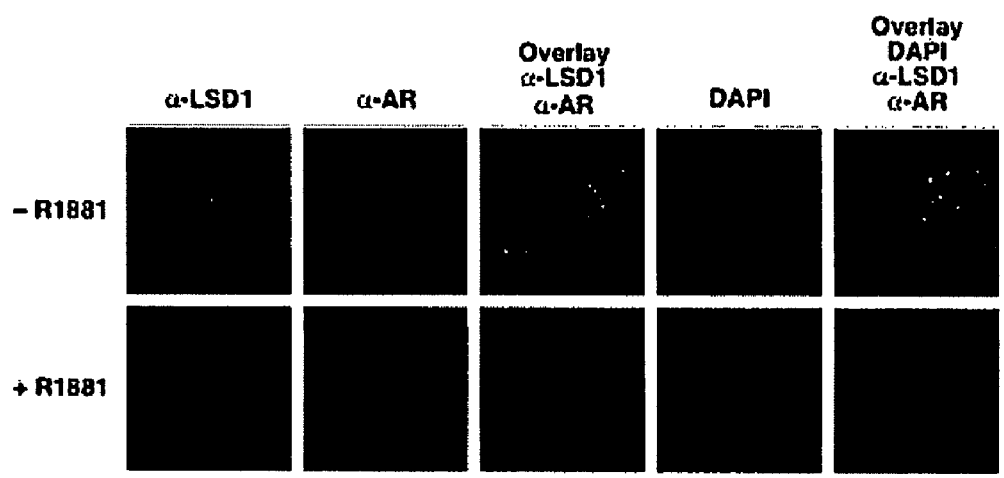

To examine the expression pattern of LSD1, there were performed Northern blot analyses. LSD1 mRNA is ubiquitously expressed in human and murine fetal and adult tissues (FIG. 2a and data not shown) as a transcript of 3.3 kb (FIG. 6a). To investigate LSD1 localisation in prostate and prostate tumours, there were used immunohistochemical analyses of 100 prostate cancer biopsies on tissue microarrays. As shown in FIG. 2b, LSD1 is detected in the epithelium of normal prostate and in tumour cells. Importantly, these cells also express AR (FIG. 2b) indicating that LSD1 and AR co-localise.

Next, the sub-cellular localisation of endogenous LSD1 and AR in human LNCaP prostate cancer cells was studied by immunofluorescence (FIG. 6b). LSD1 is present in the nucleus in the absence and presence of the AR agonist R1881. Addition of R1881 results in nuclear co-localisation of AR and LSD1. Taken together, the data show that LSD1 is a nuclear protein that co-localises with AR in androgen-sensitive tissues such as prostate.

Figure 7:
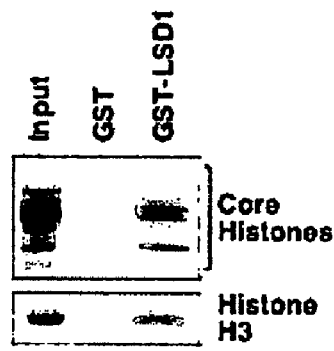
FIG. 7 shows that LSD1 interacts with chromatin. a, Coomassie blue staining reveals interaction of bacterially expressed GST-LSD1 with core histones and histone H3 in vitro. b, In vitro translated $^{35}$S-methionine labeled LSD1 interacts with sepharose coupled N-terminal tail of histone H3.
Figure 7:
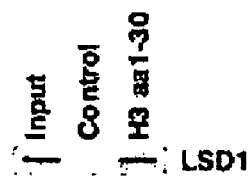

Since LSD1 was found to associate with chromatin and demethylates H3-K4 in vitro[7], it was examined whether LSD1 directly interacts with core histones. Interaction analyses demonstrated physical association with core histones in vitro (FIG. 7a). Furthermore, the analyses show that LSD1 interacts with the N-terminal tail of histone H3 (FIG. 7b).

To determine whether LSD1 and AR associate with chromatin in vivo, LNCaP cells treated with or without (i.e. untreated) R1881 were subjected to chromatin immunoprecipitation (ChIP). As shown in FIG. 3a, genomic DNA corresponding to the androgen response elements (ARE I+II and ARE III) located in the promoter and enhancer of the prostate specific antigen (PSA) gene, respectively, was immunoprecipitated in a ligand-dependent manner with α-AR antibodies. Genomic DNA derived from a region between the enhancer and promoter was not enriched (FIG. 3a). Association of LSD1 with the chromatinized PSA promoter is specific, since DNA from neither exon 4 of the PSA gene nor the promoters of the GAPDH and U6 genes is enriched (FIG. 3a).

To demonstrate that LSD1 and AR form ligand-dependent complexes on chromatinized AREs, agonist-treated LNCaP cells were subjected to sequential chromatin immunoprecipitation (Re-ChIP), first with an α-AR antibody and next with either α-LSD1 antibody or control α-rabbit IgG. Importantly, both ARE containing regions were enriched, demonstrating that LSD1 and AR form a ligand-dependent complex on chromatin (FIG. 3a).

Since PSA gene expression is induced by AR, the methylation levels of repressive histone marks were analysed, such as histone 3 at lysine 9 (H3-K9), histone 3 at lysine 27 (H3-K27), and histone 4 at lysine 20 (H4-K20). Stimulation of LNCaP cells with R1881 results in androgen-induced transcription and is accompanied by a robust decrease in mono-, di-, and trimethyl H3-K9 at the PSA promoter (FIG. 3b). In addition, there was observed a ligand-dependent decrease in dimethyl H4-K20, whereas mono- and trimethyl H4-K20 and methylation levels of H3-K27 remain unchanged (FIG. 8).

Since LSD1 is an AO that catalyses demethylation, a test was conducted whether monoamine oxidase inhibitors such as pargyline (N-methyl-N-2-propynylbenzylamine), clorgyline (N-methyl-N-propargyl-3-(2,4-dichlorophenoxy-) propylamine) or deprenyl (=seregeline; (R)-(−)-N,2-dimethyl-N-2-propynylphenethylamine) might interfere with LSD1 demethylation function. Importantly, pargyline blocks demethylation of mono- and dimethyl H3-K9 during androgen-induced transcription, whereas methylation levels of trimethyl H3-K9 and the methylation status of H3-K27 and, H4-K20 remain unchanged (FIG. 3b and FIG. 8). Interestingly, methylation of histone H3 at lysine 4 (H3-K4) is not altered in the presence of R1881 and not influenced by pargyline in vivo (FIG. 3b).

To prove that LSD1 executed the ligand-dependent demethylation of mono- and dimethyl H3-K9, we designed various siRNAs directed against LSD1 or an unrelated control (FIG. 9). Transfection of LNCaP cells leads to efficient and specific down-regulation of endogenous LSD1 but does not affect the level of endogenous AR (FIG. 3c). LSD1 knockdown blocks ligand-dependent demethylation of mono- and dimethyl H3-K9, but not that of trimethyl H3-K9 (FIG. 3c). The amount of total H3 on the PSA promoter is not influenced by the LSD1 knockdown (FIG. 3c).

To further validate that the LSD1/AR complex removes H3-K9 dimethyl marks in the presence of R1881, there was established a demethylation assay in vitro. Tandem affinity purified (TAP) LSD1 (FIG. 3d) was incubated in the presence or absence of AR (FIG. 3d) was incubated in the presence of R1881 with HeLa nucleosomes as the substrate. The TAP-LSD1/AR complex demethylated dimethyl H3-K9 in vitro, whereas TAP-LSD1 or the TAP control failed to do so. The methylation status of the trimethyl H3-K9 control is not altered (FIG. 3d). An addition of pargyline blocked the demethylation of dimethyl H3-K9 by the TAP-tagged LSD1/AR complex (FIG. 3d). Thus, the in vitro assay proofs that the LSD1/AR complex directly and specifically demethylates H3-K9 and that the demethylation is blocked by pargyline.

Taken together, these data show the ligand-dependent association of LSD1 and AR on chromatinized AREs at the promoter of the PSA gene and the specific demethylation of the repressive histone marks mono- and dimethyl H3-K9.

Next, there were performed transient transfection assays to test whether LSD1 modulates the transcriptional activity of AR. Co-expression of LSD1 and AR results in a strong ligand-dependent activation of an MMTV-luciferase reporter (FIG. 4a), which is not observed with deletion mutant LSD1ΔAO or in the absence of either ligand or AR (FIG. 4a and FIG. 10). Stimulation of AR activity by LSD1 is potent in different cell lines, and both AR-responsive minimal, synthetic and complex promoters were activated by LSD1 in a ligand-dependent manner (FIG. 10b, 10c). LSD1 does not affect the transcriptional activity of the related steroid hormone receptors, indicating that stimulation of AR is selective (FIG. 10h).

Furthermore, it is demonstrated that the AO domain (LSD1 247-852) of LSD1 suffices to stimulate AR- and ligand-dependent reporter gene activity (FIG. 4b).

Since displacement of repressive histone marks by LSD1 increases AR-dependent gene expression, inhibition of LSD1 should reduce AR activity. Consequently, monoamine oxidase inhibitors such as pargyline, clorgyline, and deprenyl severely impair LSD1-induced activation of AR (FIG. 4c). Importantly, in LNCaP cells, which express endogenous AR, only androgen-dependent but not unrelated reporters such as TK-LUC are inhibited by pargyline thus demonstrating specificity (FIG. 10j). Pargyline does not influence activity of other nuclear receptors (FIG. 10k). Moreover, qRT-PCR analyses demonstrate that pargyline also blocks the androgen-induced expression of the endogenous PSA gene in LNCaP cells (FIG. 4d).

Figure 4:
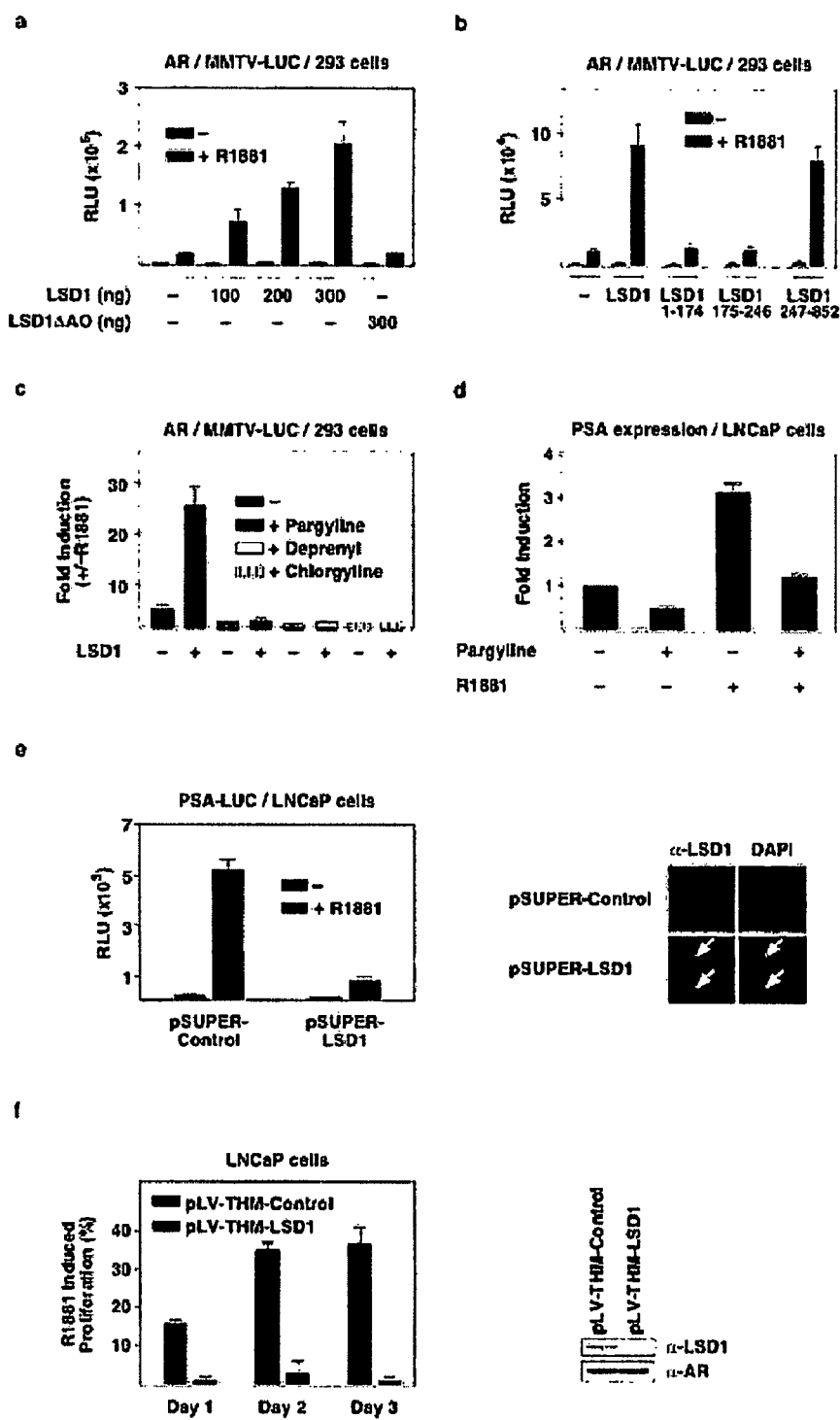
Figure 5:
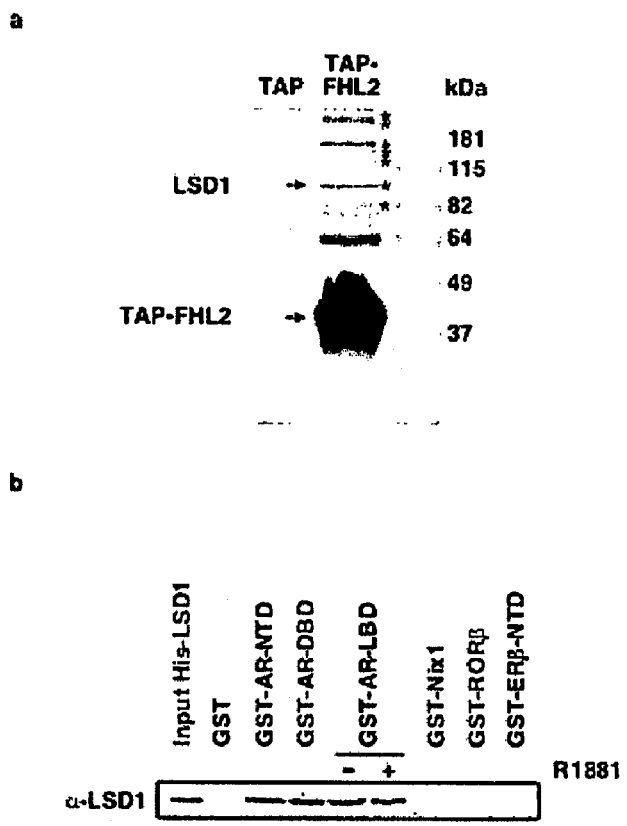

Next, endogenously expressed LSD1 was efficiently used in LNCaP cells by vector (pSUPER-LSD1) mediated RNAi (FIG. 4e). Paralleling LSD1 knockdown, a significant ligand-dependent decrease of PSA-LUC reporter gene expression was observed (FIG. 4e), whereas expression of the unrelated TK-LUC is not influenced (data not shown). To address whether LSD1 governs androgen-dependent cell growth, LNCaP cells were infected with a lentivirus (pLV-THM-LSD1) expressing siRNA directed against LSD1. Infection with pLV-THM-LSD1 causes efficient and specific down-regulation of endogenous LSD1 but does not affect the level of endogenous AR (FIG. 4). Importantly, when compared to cells transduced with the pLV-THM-control virus, androgen-induced proliferation of LNCaP cells is dramatically inhibited by pLV-THM-LSD1 mediated LSD1 knockdown (FIG. 4f). These results show the physiological importance of LSD1 in the control of androgen-induced gene regulation and cell proliferation.

In summary, the above data demonstrate that AR function is controlled by the demethylase LSD1. LSD1 and AR associate at chromatinized AREs of AR target genes a ligand-dependent manner, which results in concomitant demethylation of the repressive histone marks mono- and dimethyl H3-K9. LSD1 has been described as a component of co-repressor complexes[8-11] and a recent model proposes that LSD1 represses transcription of genes silenced by Co-REST due to demethylation of the activating histone marks on H3-K4[7]. However, when complexed with AR, LSD1 demethylates the repressing histone marks mono- and dimethyl H3-K9 and thereby promotes gene activation. Thus, depending on the specific interacting partners, LSD1 action might result in either gene silencing or activation. Of importance is the observation that inhibitors such as pargyline control the demethylase activity of LSD1 and thereby regulate AR. Thus, specific modulation of LSD1 activity might be a promising therapeutic target in tissues such as brain, testis, prostate where AR plays a pivotal physiological role.

Methods

Plasmids

The following plasmids were described previously: pSG5-AR, PR, CMX-Flag, GST-AR-NTD, GST-AR-DBD, GST-AR-LBD, GST-ERβ-NTD, MMTV-LUC, and TK-LUC[17]; ARE$_{2X}$-TATA-LUC, ARE$_{2X}$-TK-LUC[21]; SIp-ARU-TATA-LUC[22]; PSA-LUC[23]; pLV-THM (http://www.tronolab.unige.ch/); pSUPER[24]; GST-Nix1, RARα, ERα, and TRβ[25]; βRE-LUC, TREp-LUC, and ERE$_{2X}$-TATA-LUC[26]. To construct CMX-Flag-LSD1, CMX-Flag-LSD1 1-174, CMX-Flag-LSD1 175-246, and CMX-Flag-LSD1 247-854, CMX-Flag-LSD1Δ281-360, CMX-Flag-LSD1ΔAO (LSD1 1-247) and GST-RORβ (RORβaa76-459), the corresponding fragments were amplified by PCR and inserted into CMX-Flag or pGEX4T-1. pSUPER-control, pSUPER-LSD1 and pLV-THM-LSD1 were constructed according to (http://www.tronolab.unige.ch/) and as published[24]. To construct TAP-LSD1 and TAP-FHL2, the corresponding fragments were amplified by PCR and inserted into a modified pCMX expression plasmid containing an N-terminal TAP tag (TAP). Sequences can be obtained upon request.

Immunofluorescence

Cells were analysed essentially as described[13]. Primary antibody staining was performed with the indicated dilutions: α-AR 441 (1:500) and α-LSD1 (1:500). Sub-cellular localisation was visualised using secondary Alexa Fluor 488- and 546-labelled antibodies (1:6000; Molecular Probes). Nuclei were stained with 1 µg/ml DAPI (Roche).

In Vitro Pull-Down Assays

Figure 1:
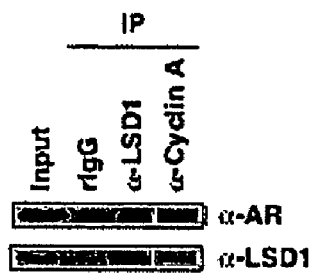
Figure 1:
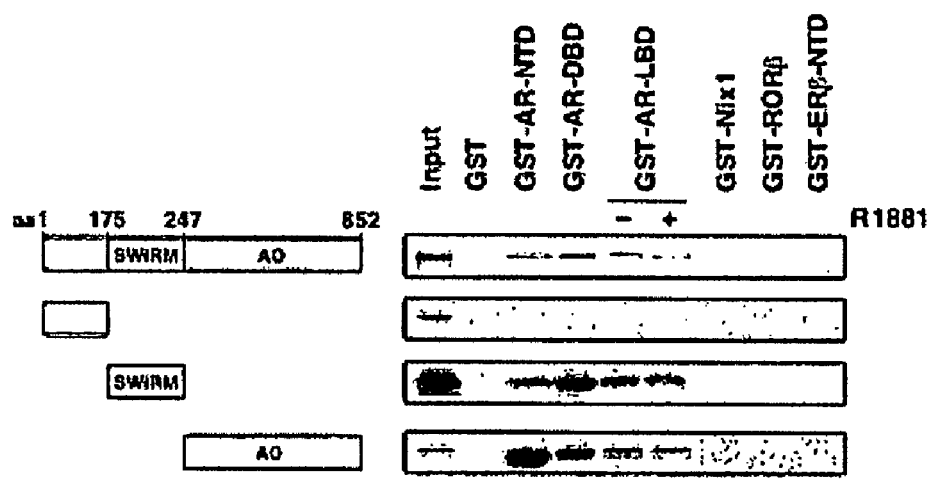

GST pull-down assays were performed with equal amounts of GST or GST fusion proteins as described[17] using buffer containing either 150 mM KCl, 0.15% NP40 (FIG. 1b) or 600 mM KCl, 0.3% NP40 (FIG. 7a). Pull-downs with sepharose coupled histone H3 tail were performed as described[27] in 20 mM Tris pH 8.5, 150 mM NaCl, 0.5% NP40. 10% of the in vitro translated proteins were loaded as input.

mRNA Analyses

Northern blot analyses were performed with a Human Multiple Tissue Expression Array and a Human Multiple Tissue Northern Blot (BD Biosciences Clontech) with an LSD1-specific probe spanning either bp 1-741 or bp 1-2556, labelled with StripEZ (Ambion), and hybridized as recommended.

Tandem Affinity Purification

TAP purification was essentially performed as described[28]. 293 cells transfected with either TAP-tag-FHL2 (TAP-FHL2) or control TAP-tag (TAP) were lysed in buffer A (20 mM HEPES/KOH pH 7.9, 420 mM NaCl, 1.5 mM MgCl$_2$, 10 mM KCl, 25% Glycerol, 0.5 mM DTT, 0.1% NP-40, 0.1 mM EDTA, 50 mM NaF, 0.2 mM $Na_3VO_4$, and Complete® protease inhibitor cocktail). TAP-tagged proteins were bound to IgG-sepharose (GE-Healthcare) in salt-adjusted buffer A (150 mM NaCl) at 4° C. over night followed by repeated washing. Bound complexes were relieved from IgG-sepharose by TEV-protease (100 U, Invitrogen) in TEV buffer (10 mM TrisHCl pH 8.0, 150 mM NaCl, 0.1% NP40, 1 mM DTT, 1 mM EDTA). CBP-containing complexes were immobilized on a Calmodulin affinity resin (Stratagene) for 4 h at 16° C. Complexes were washed five times with CBP-buffer (10 mM TrisHCl pH 8.0, 150 mM NaCl, 0.1% NP40, 1 mM MgAcetate, 1 mM Imidazole, 10 mM β-mercaptoethanol, 2 mM $CaCl_2$) and eluted with CBP buffer containing 10 mM EGTA instead of $CaCl_2$). Protein complexes were size separated by SDS-PAGE, visualized by Coomassie stain and identified by MALDI-TOF/TOF (Explora AG, Darmstadt, Germany).

Immunohistochemistry

Polyclonal rabbit-α-LSD1 antibody was generated according to standard procedures. Stainings were performed using a protocol[13] for antigen retrieval and indirect immunoperoxidase. α-AR 441 (Santa Cruz) and α-LSD1 were used at a dilution of 1:75 and 1:500, rabbit IgG and mouse IgG (1:500; Dako) were used as secondary antibodies and immunoreactions were visualised with the ABC-complex diluted 1:50 in PBS (Vectastain, Vector).

Cell Culture and Transfections 293 and CV-1 cells were cultured and transfected as described[12]. LNCaP cells were cultured in phenol-red-free RPMI1640 supplemented with 10% double-stripped fetal calf serum (dsFCS) and transfected with Effectene (Qiagen). The following amounts per well were used: MMTV-LUC, $ARE_{2x}$-TATA-LUC, $ARE_{2x}$-TK-LUC, TK-LUC, TREp-LUC, β-RE-LUC, $ERE_{2x}$-TATA-LUC, PSA-LUC, Slp-ARU-TATA-LUC 500 ng each, 25 ng expression plasmids for AR, PR, ERα, RARα, and TRβ; 500 to 700 ng expression plasmids for LSD1 1-174, LSD1 175-246, LSD1 247-852, LSD1Δ281-360, LSD1ΔAO, pSUPER-control, and pSUPER-LSD1; 100 to 700 ng expression plasmids for LSD1 were transfected per well. Chemicals were obtained as indicated: pargyline (Sigma); deprenyl and clorgyline (ICN Biomedicals Inc.); R1881, T3, $E_2$, all-trans RA and R5020 (Schering AG, Berlin). Cells were treated with or without $10^{-10}$ M R1881, $10^{-8}$ M R5020, $10^{-9}$ M $E_2$, $10^{-7}$ M T3, $10^{-6}$ M all-trans RA, $3 \times 10^{-3}$ M pargyline, $1 \times 10^{-3}$ M deprenyl, or $1 \times 10^{-4}$ M clorgyline for 18 hours as indicated. Luciferase activity was assayed as described[9]. All experiments were repeated at least five times in duplicate.

Chromatin Immunoprecipitation

ChIP experiments were performed essentially as described[14]. LNCaP cells were treated for 18 hours with or without pargyline and for 210 min with or without $10^{-8}$ M R1881 as indicated. LNCaP cells were transfected three days before harvesting for ChIP with or without siRNA (Qiagen) following the manufacture's instructions. Immunoprecipitation was performed with specific antibodies (α-monoMeK9H3, α-diMeK9H3, α-triMeK9H3, α-monoMeK4H3, α-diMeK4H3, α-triMeK4H3, α-H3 (abcam), α-LSD1, and α-AR PG21 (Upstate Biotechnology) on GammaBind™-Sepharose 4B (GE-Healthcare). For PCR, 1-5 μl out of 50 μl DNA extract was used. For Re-ChIP assays, immunoprecipitations were sequentially washed with TSE I, TSE II, buffer III, and TE[14]. Complexes were eluted by incubation with 10 mM DTT at 37° C. for 30 min, diluted 50 times with dilution buffer[14] followed by a second immunoprecipitation with the indicated antibody. Primer sequences were as follows: exon 4, PSA (+3909/+4067) 5'-GTGTGTGGAC-CTCCATGTTATT-3' (SEQ ID NO: 21) and 5'-CCACTCAC-CTTTCCCCTCAAG-3' (SEQ ID NO: 22); middle, PSA (−2223/−1951) 5'-TGGGTTGGGTCAGGTTTTGGTT-3' (SEQ ID NO: 23) and 5'-TCTTCCCCTGTTTCTAGT-TGAGTG-3' (SEO ID NO: 24); PCR primers for ARE I+II (PSA (−459/−121)) and ARE III (PSA (−4288/−3922)), GAPDH, and U6 have been previously described[7, 15, 16].

Co-Immunoprecipitation Assays and Western Blot Analyses

Experiments were performed essentially as described[17]. Immunoprecipitations from extracts of murine testis were performed in the presence of $1 \times 10^{-9}$ M R1881 with either α-LSD1, α-cyclin A[17] antibodies, or rabbit IgG. Western blots were decorated as indicated. α-AR (N20, Santa Cruz) was used. 10% of testis extract was loaded as input.

Cell Proliferation Assay pLV-THM-control and pLV-THM-LSD1 were used to produce recombinant lentiviruses to infect LNCaP cells as described[18]. The infected cells were cultured for 72 hours in medium supplemented with 10% dsFCS. $0.3 \times 10^4$ cells were plated in a 96-well plate with or without $10^{-7}$ M R1881. The cell proliferation Elisa BrdU Colorimetric Assay (Roche) was performed according to the manufacturer's instructions. The experiments were repeated three times in quadruplet.

qRT-PCR and Statistical Analysis

DNAseI-treated RNA isolated using RNAwiz (Ambion) was used for reverse transcription. Quantitative PCR was performed in an ABI PRISM 7700 sequence detector. Product formation was detected by incorporation of SYBR Green I using ROX as a passive reference (ABgene). The expression ratios of the analyzed cDNAs were related to the normalized $C_p$ of the housekeeping gene GAPDH in control and sample. The following primers were used: GAPDH: 5'-GAAGGT-GAAGGTCGGACTC-3' (SEQ ID NO: 25); 5'-GAAGATG-GTGATGGGATTTC-3' (SEQ ID NO: 26); PSA: 5'-CACCT-GCTCGGGTGATTCTG-3' (SEQ ID NO: 27); 5'-CCACTTCCGGTAATGCACCA-3' (SEQ ID NO: 28). Statistical analysis for qPCR was performed by group-wise comparison based on PCR efficiencies and the mean crossing point deviation between sample and control group using Relative Expression Software Tool[19]. Experiments were repeated and analysed three times.

Demethylase Assay

The demethylation assay was essentially performed as described[7]. TAP-tagged proteins were bound to IgG-sepharose, washed and incubated in buffer 1 supplemented with 10 mM ATP, $10^{-9}$ M R1881 with or without $1 \times 10^{-3}$ M pargyline and 1 μg of nucleosomes purified from HeLa cells[16] for 6 hours at 37° C. The reaction mixture was analyzed by SDS-PAGE followed by Western blotting using antibodies as indicated.

REFERENCES

1. Breslow, M., Chan, C. W., Dhom, G. et al. Latent carcinoma of prostate at autopsy in seven areas. Int. J. Cancer. 1977, 20:680-688
2. Cato, A. C. and Peterzierl, H. The androgen receptor as a mediator of gene expression and signal transduction pathways. Trends Endocrinol. Metab. 1998, 9, 150-154.
3. Denmeade. S. R. and Isaacs, J. T. A history of prostate cancer treatment. Nat. Rev. Cancer 2002, 5, 389-96
4. Waterbor, J. W. and Bueschen, A. J. Prostate Cancer Screening (United States). Cancer Causes Control 1995, 6:267-274

5. Glass, C. K. & Rosenfeld, M. G. The coregulator exchange in transcriptional function of nuclear receptors. *Genes Dev.* 14, 121-141 (2000).
6. Strahl, B. D. & Allis, C. D. The language of covalent histone modifications. *Nature* 403, 41-45 (2000).
7. Shi, Y. et al. Histone demethylation mediated by the nuclear amine oxidase homolog LSD1. *Cell* 119, 941-953 (2004).
8. Shi, Y. et al. Coordinated histone modifications mediated by a CtBP co-repressor complex. *Nature* 422, 735-738 (2003).
9. Hakimi, M. A. et al. A candidate X-linked mental retardation gene is a component of a new family of histone deacetylase-containing complexes. *J. Biol. Chem.* 278, 7234-7239 (2003).
10. Hakimi, M. A. et al. A core-BRAF35 complex containing histone deacetylase mediates repression of neuronal-specific genes. *Proc. Natl Acad. Sci. USA* 99, 7420-7425 (2002).
11. Elmer, S. et al. Loss of spr-5 bypasses the requirement for the *C. elegans* presenilin sel-12 by derepressing hop-1. *EMBO J.* 21, 5787-5796 (2002).
12. Müller, J. M. et al. FHL2, a novel tissue-specific coactivator of the androgen receptor. *EMBO J.* 19, 359-369 (2000).
13. Müller, J. M. et al. The transcriptional coactivator FHL2 transmits Rho signals from the cell membrane into the nucleus. *EMBO J.* 21, 736-748 (2002).
14. Shang, Y., Myers, M. & Brown, M. Formation of the androgen receptor transcription complex. *Mol. Cell.* 9, 601-610 (2002)
15. Shatkina, L. et al. The cochaperone Bag-1 L enhances androgen receptor action via interaction with the NH2-terminal region of the receptor. *Mol. Cell. Biol.* 23, 7189-7197 (2003).
16. Kang, Z., Pirskanen, A., Jänne, O. A. & Palvimo, J. J. Involvement of proteasome in the dynamic assembly of the androgen receptor transcription complex. *J. Biol. Chem.* 277, 48366-48371 (2002).
17. Metzger, E. et al. A novel inducible transactivation domain in the androgen receptor: implications for PRK in prostate cancer. *EMBO J.* 22, 270-280 (2003).
18. Wiznerowicz, M. & Trono, D. Conditional suppression of cellular genes: lentivirus vector-mediated drug-inducible RNA interference. *J. Virol.* 77, 8957-8961 (2003).
19. Pfaffl, M. W., Horgan, G. W. & Dempfle, L. Relative expression software tool (REST) for group-wise comparison and statistical analysis of relative expression results in real-time PCR. *Nucleic Acids Res.* 30, e36 (2002).
20. O'Neill, T. E., Roberge, M. & Bradbury E. M. Nucleosome arrays inhibit both initiation and elongation of transcripts by bacteriophage T7 RNA polymerase. *J. Mol. Biol.* 223, 67-78 (1992).
21. Schüle, R. et al. Functional antagonism between oncoprotein c-Jun and the glucocorticoid receptor. *Cell* 62, 1217-1226 (1990).
22. Verrijdt, G. et al. Functional interplay between two response elements with distinct binding characteristics dictates androgen specificity of the mouse sex-limited protein enhancer. *J. Biol. Chem.* 277, 35191-35201 (2002).
23. Sun, Z., Pan, J. & Balk, S. P. Androgen receptor-associated protein complex binds upstream of the androgen-responsive elements in the promoters of human prostate-specific antigen and kallikrein 2 genes. *Nucleic Acids Res.* 25, 3318-3325 (1997).
24. Brummelkamp, T. R., Bernards, R. & Agami, R. A system for stable expression of short interfering RNAs in mammalian cells. *Science* 296, 550-553 (2002).
25. Greiner, E. F. et al. Differential ligand-dependent protein-protein interaction between nuclear receptors and a neuronal-specific cofactor. *Proc. Natl Acad. Sci. USA* 97, 7160-7165 (2000).
26. Schüle, R. et al. Jun-Fos and receptors for vitamin A and D recognize a common response element in the human osteocalcin gene. *Cell* 61, 497-504 (1990).
27. Schneider, R. et al. Direct binding of INHAT to H3 tails disrupted by modifications. *J. Biol. Chem.* 279, 23859-23862 (2004).
28. Rigaut, G. et al. A generic protein purification method for protein complex characterization and proteome exploration. *Nat. Biotechnol.* 17, 1030-1032 (1999).
29. Bocker, T., Bittinger, A., Wieland, W., Buettner, R., Fauser, G., Hofstaedter, F., Rüschoff, In vitro and ex vivo expression of nucleolar proteins B23 and p120 in benign and malignant epithelial lesions of the prostate. *J. Modern Pathology* 8: 226-31, 1995.

The invention claimed is:

1. A method for identifying a patient having high risk prostate carcinomas, said method comprising:
   (1) obtaining a biological material comprising prostate cancer tissue, prostate cancer cells, and/or protein extracts from prostate cancer tissue from said patient;
   (2) immunostaining said prostate cancer tissues, prostate cancer cells, and/or protein extracts from prostate cancer tissue with an anti-LSD1 antibody that binds to an epitope in the LSD1 protein of a mammal; and
   (3) quantifying the amount of LSD1 in said prostate cancer tissues, prostate cancer cells, and/or protein extracts from prostate cancer tissue, wherein detection of LSD1 overexpression therein indicates that the patient has a high risk prostate carcinoma.

2. The method according to claim 1, wherein the antibody is directed to the epitope (SEQ ID NO: 4)
AGPGTAGGSENGSEVAAQPAGLSGPAEVGPGAVGERTPRKKEPPRASPPG
GLAEPPGSAGPQAGPTVVPGSATPMETGIAETPEGRRTSRRKRAKVEYRE
MDESLANLSEDEYYSE.

3. The method according to claim 1, wherein the quantifying is direct or indirect.

4. The method of claim 3, wherein the direct quantifying is chosen from spectrometric methods, chromatographic methods, and combinations thereof.

5. The method of claim 3, wherein the indirect quantifying is chosen from immunohistochemistry, immunocytochemistry, ELISA technologies, and combinations thereof.

6. The method according to claim 1, wherein the mammal is a human.

* * * * *

```
                            SEQUENCE LISTING

<160> NUMBER OF SEQ ID NOS: 28

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      target oligonucleotide for siRNA-1

<400> SEQUENCE: 1
cggacaagct gttcctaaa                                                   19

<210> SEQ ID NO 2
<211> LENGTH: 19
<212> TYPE: DNA
<213> ORGANISM: Artificial Sequence
<220> FEATURE:
```

-continued

```
<223> OTHER INFORMATION: Description of Artificial Sequence: Synthetic
      target oligonucleotide for siRNA-2

<400> SEQUENCE: 2
gaactccatc agcaataca                                                  19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      target oligonucleotide for siRNA-3

<400> SEQUENCE: 3
cacaaggaaa gctagaaga                                                  19

<210> SEQ ID NO 4
<211> LENGTH: 116
<212> TYPE: PRT
<213> ORGANISM: Homo sapiens

<400> SEQUENCE: 4
```

Ala Gly Pro Gly Thr Ala Gly Gly Ser Glu Asn Gly Ser Glu Val Ala
1               5                   10                  15

Ala Gln Pro Ala Gly Leu Ser Gly Pro Ala Glu Val Gly Pro Gly Ala
            20                  25                  30

Val Gly Glu Arg Thr Pro Arg Lys Lys Glu Pro Pro Arg Ala Ser Pro
        35                  40                  45

Pro Gly Gly Leu Ala Glu Pro Pro Gly Ser Ala Gly Pro Gln Ala Gly
    50                  55                  60

Pro Thr Val Val Pro Gly Ser Ala Thr Pro Met Glu Thr Gly Ile Ala
65                  70                  75                  80

Glu Thr Pro Glu Gly Arg Arg Thr Ser Arg Arg Lys Arg Ala Lys Val
                85                  90                  95

Glu Tyr Arg Glu Met Asp Glu Ser Leu Ala Asn Leu Ser Glu Asp Glu
            100                 105                 110

Tyr Tyr Ser Glu
        115

```
<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      sense oligonucleotide of siRNA-1

<400> SEQUENCE: 5
cggacaagcu guuccuaaau u                                               21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      sense oligonucleotide of siRNA-2

<400> SEQUENCE: 6
gaacuccauc agcaauacau u                                               21
```

```
<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      sense oligonucleotide of siRNA-3

<400> SEQUENCE: 7
cacaaggaaa gcuagaagau u                                             21

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      sense oligonucleotide of siRNA-4

<400> SEQUENCE: 8
gugucaauuu guucgggcau uu                                            22

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      sense oligonucleotide of siRNA-5

<400> SEQUENCE: 9
gcgaggcgag gcaaggcuuu u                                             21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cttgctatga gaacaaatt                                                19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aacggacaag ctgttcctaa a                                             21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aagaactcca tcagcaatac a                                             21

<210> SEQ ID NO 13
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aacacaagga aagctagaag a                                              21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aagtgtcaat tgttcgggc at                                              22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagcgaggcg aggcaaggct t                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uuuaggaaca gcuuguccgu u                                              21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uguauugcug auggaguucu u                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ucuucuagcu uuccuugugu u                                              21

<210> SEQ ID NO 19
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
augcccgaac aaauugacac uu                                             22

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aagccuugcc ucgccucgcu u                                              21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtgtgtggac ctccatgtta tt                                             22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccactcacct ttcccctcaa g                                              21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgggttgggt caggttttgg tt                                             22

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcttcccctg tttctagttg agtg                                           24

<210> SEQ ID NO 25
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
gaaggtgaag gtcggactc                                                   19

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaagatggtg atgggatttc                                                  20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cacctgctcg ggtgattctg                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccacttccgg taatgcacca                                                  20
```